(12) United States Patent
Naganathan et al.

(10) Patent No.: US 8,426,415 B2
(45) Date of Patent: Apr. 23, 2013

(54) HUMAN ADAM-10 INHIBITORS

(75) Inventors: Sriram Naganathan, San Jose, CA (US); JoAnn Wilson, San Francisco, CA (US); Daniel A. Dickman, San Ramon, CA (US)

(73) Assignee: Symphony Evolution, Inc., Rockville, MD (US)

( * ) Notice: Subject to any disclaimer, the term of this patent is extended or adjusted under 35 U.S.C. 154(b) by 0 days.

(21) Appl. No.: 12/682,874

(22) PCT Filed: Oct. 15, 2008

(86) PCT No.: PCT/US2008/080021
§ 371 (c)(1), (2), (4) Date: Aug. 31, 2010

(87) PCT Pub. No.: WO2009/052200
PCT Pub. Date: Apr. 23, 2009

(65) Prior Publication Data
US 2011/0003812 A1    Jan. 6, 2011

Related U.S. Application Data

(60) Provisional application No. 60/980,352, filed on Oct. 16, 2007.

(51) Int. Cl.
*A61K 31/497* (2006.01)
*A61K 31/4965* (2006.01)
*C07D 295/00* (2006.01)

(52) U.S. Cl.
USPC ............ 514/252.12; 514/255.01; 514/255.02; 544/383

(58) Field of Classification Search ............. 514/252.12, 514/255.01, 255.02; 544/383
See application file for complete search history.

(56) References Cited

U.S. PATENT DOCUMENTS
5,753,653 A    5/1998    Bender et al.
6,333,324 B1   12/2001   Neya et al.

FOREIGN PATENT DOCUMENTS
WO    97/20824 A1    6/1997
WO    03/106381 A2   12/2003

OTHER PUBLICATIONS

Chen, Jian Jeffrey et al: "Design and synthesis of orally active inhibitors of TNF synthesis as anti-rheumatoid arthritis drugs" Bioorganic & Medicinal Chemistry Letters, 13(22), 3951-3954 CODEN: BMCLE8; ISSN: 0960-894X, 2003, XP002524008 p. 3951-p. 3953; table 2.

*Primary Examiner* — Samira Jean-Louis
(74) *Attorney, Agent, or Firm* — McDonnell Boehnen Hulbert & Berghoff LLP

(57) ABSTRACT

Magnesium salts/complexes of compounds useful for inhibiting the ADAM-IO protein and methods of making and purifying them are provided. Further provided are compositions comprising magnesium salts/complexes of the compounds in combination with a pharmaceutically acceptable carrier. The compounds well as such compositions comprising them are useful for the treatment of cancer, arthritis, diseases related to angiogenesis, such as renal diseases, heart diseases, such as heart failure, atherosclerosis, and stroke, inflammation, ulcer, infertility, scleroderma, endometriosis, mesothelioma, and diabetes. In addition, methods of treating forms of cancer, arthritis, and diseases related to angiogenesis in which ADAM-10 plays a critical role are provided.

13 Claims, No Drawings

HUMAN ADAM-10 INHIBITORS

CROSS-REFERENCE TO RELATED APPLICATIONS

This application claims priority to U.S. Provisional Patent Application Ser. No. 60/980,352, filed Oct. 16, 2007, which is hereby incorporated by reference in its entirety.

BACKGROUND OF THE DISCLOSURE

1. Field of the Disclosure

Compounds useful for inhibiting ADAM-10 (also known as human Kuzbanian) are provided. Representative compound includes the magnesium salt/complex of 4-(4-(4-chlorophenoxy)-3,5-difluorophenylsulfonyl)-3-(hydroxycarbamoyl)piperazine-1-carboxylic acid (R)-2-methoxyethyl ester. Also provided are salts/complexes and compositions thereof, useful in the treatment of cancer, arthritis, diseases related to angiogenesis, such as renal diseases, heart diseases, such as heart failure, atherosclerosis, and stroke, inflammation, ulcer, infertility, scleroderma, endometriosis, mesothelioma, and diabetes. Further provided are methods of preparing and purifying the magnesium salts/complexes of the compounds useful for inhibiting the ADAM-10 protein.

2. Summary of the Related Art

Cell-cell interactions play an important role in regulating cell fate decisions and pattern formation during the development of multicellular organisms. One of the evolutionarily conserved pathways that plays a central role in local cell interactions is mediated by the transmembrane receptors encoded by the Notch (N) gene of *Drosophila*, the lin-12 and glp-1 genes of *C. elegans*, and their vertebrate homologs (reviewed in Artavanis-Tsakonas, S., et al. (1995) Notch Signaling. Science 268, 225-232), collectively hereinafter referred to as NOTCH receptors. Several lines of evidence suggest that the proteolytic processing of NOTCH receptors is important for their function. For example, in addition to the full-length proteins, antibodies against the intracellular domains of NOTCH receptors have detected C-terminal fragments of 100-120 kd; see, e.g., Fehon, R. G., et al. (1990). Cell 61, 523-534; Crittenden, S. L., et al. (1994). Development 120, 2901-2911; Aster, J., et al. (1994) Cold Spring Harbor Symp. Quant. Biol. 59, 125-136; Zagouras, P., et al. (1995) Proc. Natl. Acad. Sci. U.S.A. 92, 6414-6418; and Kopan, R., et al. (1996). Proc. Natl. Acad. Sci. U.S.A. 93, 1683-1688. However, the mechanism(s) of NOTCH activation have been hitherto largely unknown.

During neurogenesis, a single neural precursor is singled out from a group of equivalent cells through a lateral inhibition process in which the emerging neural precursor cell prevents its neighbors from taking on the same fate (reviewed in Simpson, P. (1990). Development 109, 509-519). Genetic studies in *Drosophila* have implicated a group of "neurogenic genes" including N in lateral inhibition. Loss-of-function mutations in any of the neurogenic genes result in hypertrophy of neural cells at the expense of epidermis (reviewed in Campos-Ortega, J. A. (1993) In: The Development of *Drosophila melanogaster* M. Bate and A. Martinez-Arias, eds. pp. 1091-1129. Cold Spring Harbor Press.).

Rooke, J., Pan, D. J., Xu, T. and Rubin, G. M. (1996). Science 273, 1227-1231, discloses neurogenic gene family, kuzbanian (kuz). Members of the KUZ family of proteins are shown to belong to the recently defined ADAM family of transmembrane proteins, members of which contain both a disintegrin and metalloprotease domain (reviewed in Wolfsberg, T. G., et al. (1995). J. Cell Biol. 131, 275-278, see also Blobel, C. P., et al. (1992). Nature 356, 248-252, 1992; Yagami-Hiromasa, T., et al. (1995). Nature 377, 652-656; Black, R. A., et al. (1997). Nature 385, 729-733, 1997; and Moss, M. L., et al. (1997). Nature 385, 733-736; see also U.S. Pat. No. 5,922,546 and U.S. Pat. No. 5,935,792).

Genes of the ADAM family encode transmembrane proteins containing both metalloprotease and disintegrin domains (reviewed in Black and White, 1998 Curr. Opin. Cell Biol. 10, 654-659; Wolfsberg and White, 1996 Dev. Biol. 180, 389-401), and are involved in diverse biological processes in mammals such as fertilization (Cho et al., 1998 Science 281, 1857-1859), myoblast fusion (Yagami-Hiromasa et al., 1995 Nature 377, 652-656) and ectodomain shedding (Moss et al., 1997 Nature 385, 733-736; Black et al., 1997 Nature 385, 729-733; Peschon et al., 1998 Science 282, 1281-1284). The *Drosophila kuzbanian* (kuz) gene represents the first ADAM family member identified in invertebrates (Rooke et al., 1996 Science 273, 1227-1231). Previous genetic studies showed that kuz is required for lateral inhibition and axonal outgrowth during *Drosophila* neural development (Rooke et al., 1996; Farnbrough et al., 1996 PNAS.USA 93, 13233-13238.; Pan and Rubin, 1997 Cell 90, 271-280; Sotillos et al., 1997 Development 124, 4769-4779). Specifically, during the lateral inhibition process, kuz acts upstream of Notch (Pan and Rubin, 1997; Sotillos et al., 1997, which encodes the transmembrane receptor for the lateral inhibition signal encoded by the Delta gene. More recently, a homolog of kuz was identified in *C. elegans* (SUP-17) that modulates the activity of a *C. elegans* homolog of Notch in a similar manner (Wen et al., 1997 Development 124, 4759-4767).

Vertebrate homologs of kuz have been isolated in *Xenopus*, bovine, mouse, rat and human. The bovine homolog of KUZ (also called MADM or ADAM 10) was initially isolated serendipitously based on its in vitro proteolytic activity on myelin basic protein, a cytoplasmic protein that is unlikely the physiological substrate for the bovine KUZ protease (Howard et al., 1996 Biochem. J. 317, 45-50). Expression of a dominant negative form of the murine kuz homolog (mkuz) in *Xenopus* leads to the generation of extra neurons, suggesting an evolutionarily conserved role for mkuz in regulating Notch signaling in vertebrate neurogenesis (Pan and Rubin, 1997). U.S. patent application Ser. No. 09/697,854, to Pan et al., filed Oct. 27, 2000, discloses that mkuz mutant mice die around embryonic day (E) 9.5, with severe defects in the nervous system, the paraxial mesoderm and the yolk sac vasculature. In the nervous system, mkuz mutant embryos show ectopic neuronal differentiation. In the paraxial mesoderm, mkuz mutant embryos show delayed and uncoordinated segmentation of the somites. These phenotypes are similar to those of mice lacking Notch-1 or components of the Notch pathway such as RBP-Jk (Conlon et al, 1995, Development 121, 1533-1545; Oka et al., 1995), indicating a conserved role for mkuz in modulating Notch signaling in mouse development. Furthermore, no visible defect was detected in Notch processing in the kuz knockout animals. In addition to the neurogenesis and somitogenesis defect, mkuz mutant mice also show severe defects in the yolk sac vasculature, with an enlarged and disordered capillary plexus and the absence of large vitelline vessels. Since such phenotype has not been observed in mice lacking Notch-1 or RBP-Jk (Swiatek et al., 1994 Genes Dev 15, 707-719; Conlon et all 1995; Oka et al., 1995 Development 121, 3291-3301), Pan et al. determined that this phenotype reveals a novel function of mkuz that is distinct from its role in modulating Notch signaling, specifically, that kuz plays an essential role for an ADAM family disintegrin metalloprotease in mammalian angiogenesis.

Studies have suggested that selective inhibition of matrix metalloproteases is important. A number of small molecule MMPI's have progressed into the clinic for cancer and rheumatoid arthritis, for example. Inhibition of MMP-1 has been implicated as the cause of side effects such as joint pain and tendonitis when unselective TACE inhibitors were employed (see Barlaam, B. et al. *J. Med. Chem.* 1999, 42, 4890). As well, clinical trials of broad spectrum inhibitors, such as "Marimastat," have been hampered due to musculoskeletal syndrome (MSS) which manifests as musculoskeletal pain after a few weeks treatment. Inhibition of MMP-1 has been suggested as having a role in the appearance of MSS. Recent efforts in the field have been directed toward design of "MMP-1 sparing" inhibitors; for example, BA-129566 emerged as a selective inhibitor which reportedly showed no signs of MSS in phase 2 clinical trials (see Natchus, M. G. et al. *J. Med. Chem.* 2000, 43, 4948).

SUMMARY OF THE DISCLOSURE

In view of the important role of KUZ (ADAM-10) in biological processes and disease states, inhibitors of this protein are desirable, particularly small molecule inhibitors. In particular, what is needed are selective matrix metalloprotease inhibitors. Of particular use are selective ADAM-10 inhibitors, those that are "MMP-1 sparing."

Magnesium salts/complexes of compounds useful for inhibiting the ADAM-10 protein are provided. Such compounds are useful in the in vitro study of the role of ADAM-10 (and its inhibition) in biological processes. Representative compound includes the magnesium salt/complex of 4-(4-(4-chlorophenoxy)-3,5-difluorophenylsulfonyl)-3-(hydroxycarbamoyl)piperazine-1-carboxylic acid (R)-2-methoxyethyl ester.

Further provided are compositions comprising magnesium salts/complexes of compounds useful for inhibiting the ADAM-10 protein in combination with a pharmaceutically acceptable carrier. The compounds as well as such compositions comprising them are useful for the treatment of cancer, arthritis, diseases related to angiogenesis, such as renal diseases, heart diseases, such as heart failure, atherosclerosis, and stroke, inflammation, ulcer, infertility, scleroderma, endometriosis, mesothelioma, and diabetes. In addition, methods of treating forms of cancer, arthritis, and diseases related to angiogenesis in which ADAM-10 plays a critical role are provided.

Also provided are methods of preparing and purifying the magnesium salts/complexes of compounds useful for inhibiting the ADAM-10 protein.

The foregoing merely summarizes certain aspects and is not intended to be limiting. All patents, applications, and publications recited herein are hereby incorporated by reference in their entirety. Where the disclosure of the present specification is inconsistent with a patent, application, or publication incorporated by reference, the disclosure of present specification shall prevail.

DETAILED DESCRIPTION OF THE DISCLOSURE

In one aspect, a magnesium salt/complex of a compound of formula I is provided:

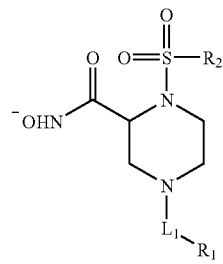

wherein
$L_1$ is —C(O)—, —S(O)$_2$—, or —(CH$_2$)$_n$—;
$R_1$ is —H, —OR$_{11}$, —(CH$_2$)$_n$R$_{11}$, —C(O)R$_{11}$, or —NR$_{12}$R$_{13}$;
$R_{11}$, $R_{12}$, and $R_{13}$ are each independently:
  a) $R_{50}$;
  b) saturated or mono- or poly-unsaturated $C_5$-$C_{14}$-mono- or fused poly-cyclic hydrocarbyl, optionally containing one or two heteroatoms per ring, wherein the saturated or mono- or poly-unsaturated $C_5$-$C_{14}$-mono- or fused poly-cyclic hydrocarbyl is optionally substituted with one or two independently selected $R_{50}$ substituents;
  c) $C_1$-$C_6$-alkyl, $C_2$-$C_6$-alkenyl, $C_2$-$C_6$-alkynyl, or —C(O)H, each of which is optionally substituted with one, two or three substituents independently selected from $R_{50}$ and saturated or mono- or poly-unsaturated $C_5$-$C_{14}$-mono- or fused poly-cyclic hydrocarbyl, optionally containing one or two heteroatoms per ring and optionally substituted with one, two or three independently selected $R_{50}$ substituents; or
  d) $R_{12}$ and $R_{13}$, together with the N to which they are covalently bound, form a $C_5$-$C_6$ heterocycle optionally containing a second heteroatom, wherein the $C_5$-$C_6$ heterocycle is optionally substituted with one or two independently selected $R_{50}$ substituents;
$R_2$ is —$R_{21}$-$L_2$-$R_{22}$;
$R_{21}$ is saturated or mono-, or poly-unsaturated $C_5$-$C_{14}$-mono- or fused poly-cyclic hydrocarbyl, optionally containing one or two heteroatoms per ring and optionally substituted with one, two, or three independently selected $R_{52}$ substituents;
$L_2$ is —O—, —C(O)—, —CH$_2$—, —NH—, —S(O)$_2$—, or a direct bond;
$R_{22}$ is saturated or mono- or poly-unsaturated $C_5$-$C_{14}$-mono- or fused poly-cyclic hydrocarbyl, optionally containing one or two heteroatoms per ring and optionally substituted with one, two, or three independently selected $R_{52}$ substituents; and
$R_{50}$ is $R_{51}$-$L_3$-(CH$_2$)$_n$—;
  $L_3$ is —O—, —NH—, —S(O)$_{0-2}$—, —C(O)—, —C(O)O—, —C(O)NH—, —OC(O)—, —NHC(O)—, —C$_6$H$_4$—, or a direct bond;
  $R_{51}$ is —H, $C_1$-$C_6$-alkyl, $C_2$-$C_6$-alkenyl, $C_2$-$C_6$-alkynyl, halo, —CF$_3$, —OCF$_3$, —OH, —NH$_2$, mono-$C_1$-$C_6$ alkyl amino, di-$C_1$-$C_6$ alkyl amino, —SH, —CO$_2$H, —CN, —NO$_2$, —SO$_3$H, or a saturated or mono- or poly-unsaturated $C_5$-$C_{14}$-mono- or fused poly-cyclic hydrocarbyl, optionally containing one or two heteroatoms per ring, wherein $R_{51}$ is optionally substituted with one, two, or three substituents selected from the group consisting of: $C_1$-$C_6$-alkyl, halo, —$CF_3$, —$OCF_3$, —OH, —$NH_2$, mono-$C_1$-$C_6$ alkyl amino, and di-$C_1$-$C_6$ alkyl amino; and $R_{52}$ is —H, $C_1$-$C_6$-alkyl, $C_2$-$C_6$-alkenyl, $C_2$-$C_6$-alkynyl, halo, —$CF_3$, —$OCF_3$, —OH, —$NH_2$, mono-$C_1$-$C_6$ alkyl amino, di-$C_1$-$C_6$ alkyl amino, —SH, —$CO_2H$, —CN, —$NO_2$, —$SO_3H$, or a saturated or mono- or poly-unsaturated $C_5$-$C_{14}$-mono- or fused poly-cyclic hydrocarbyl, optionally containing one or two heteroatoms per ring; and wherein n is 0, 1, 2, or 3;

provided that an O or S is not singly bonded to another O or S in a chain of atoms.

In one embodiment, a magnesium salt/complex of 4-(4-(4-chlorophenoxy)-3,5-difluorophenylsulfonyl)-3-(hydroxycarbamoyl)piperazine-1-carboxylic acid (R)-2-methoxyethyl ester is provided. A representative, non-limiting structure is shown below (Formula II).

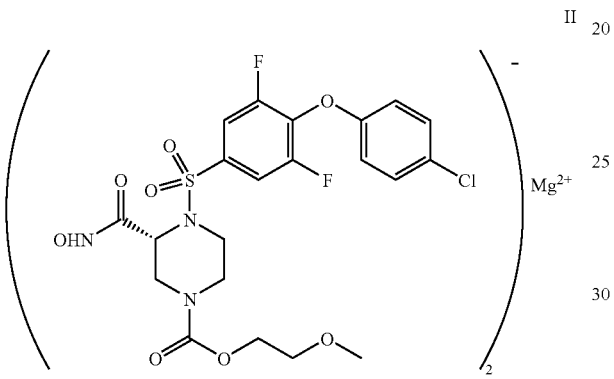

II

In one embodiment of this aspect, the magnesium salt/complex of compound of formula I is one in which:

$L_1$ is —C(O)—;
$R_1$ is —$OR_{11}$,
where $R_{11}$ is —$C_1$-$C_3$alkyl-O—$C_1$-$C_3$alkyl;
$R_2$ is —$R_{21}$-$L_2$-$R_{22}$,
where $R_{21}$ is phenyl substituted with 1, 2 or 3 halo,
$L_3$ is —O—, and
$R_{22}$ is phenyl substituted with 1, 2 or 3 halo.

In another aspect, a process for preparing a magnesium salt/complex of a compound of formula I is provided:

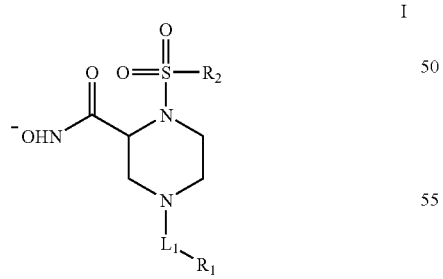

I wherein
$L_1$ is —C(O)—, —$S(O)_2$—, or —$(CH_2)_n$—;
$R_1$ is —H, —$OR_{11}$, —$(CH_2)_nR_{11}$, —$C(O)R_{11}$, or —$NR_{12}R_{13}$;
$R_{11}$, $R_{12}$, and $R_{13}$ are each independently:
a) $R_{50}$;
b) saturated or mono- or poly-unsaturated $C_5$-$C_{14}$-mono- or fused poly-cyclic hydrocarbyl, optionally containing one or two heteroatoms per ring, wherein the saturated or mono- or poly-unsaturated $C_5$-$C_{14}$-mono- or fused poly-cyclic hydrocarbyl is optionally substituted with one or two independently selected $R_{50}$ substituents;
c) $C_1$-$C_6$-alkyl, $C_2$-$C_6$-alkenyl, $C_2$-$C_6$-alkynyl, or —C(O)H, each of which is optionally substituted with one, two or three substituents independently selected from $R_{50}$ and saturated or mono- or poly-unsaturated $C_5$-$C_{14}$-mono- or fused poly-cyclic hydrocarbyl, optionally containing one or two heteroatoms per ring and optionally substituted with one, two or three independently selected $R_{50}$ substituents; or
d) $R_{12}$ and $R_{13}$, together with the N to which they are covalently bound, form a $C_5$-$C_6$ heterocycle optionally containing a second heteroatom and optionally substituted with one or two independently selected $R_{50}$ substituents;

$R_2$ is —$R_{21}$-$L_2$-$R_{22}$;

$R_{21}$ is saturated or mono-, or poly-unsaturated $C_5$-$C_{14}$-mono- or fused poly-cyclic hydrocarbyl, optionally containing one or two heteroatoms per ring and optionally substituted with one, two, or three independently selected $R_{52}$ substituents;

$L_2$ is —O—, —C(O)—, —$CH_2$—, —NH—, —$S(O)_2$—, or a direct bond;

$R_{22}$ is saturated or mono- or poly-unsaturated $C_5$-$C_{14}$-mono- or fused poly-cyclic hydrocarbyl, optionally containing one or two heteroatoms per ring, wherein the $C_5$-$C_6$ heterocycle is optionally substituted with one, two, or three independently selected $R_{52}$ substituents; and $R_{50}$ is $R_{51}$-$L_3$-$(CH_2)_n$—;
$L_3$ is —O—, —NH—, —$S(O)_{0-2}$—, —C(O)—, —C(O)O—, —C(O)NH—, —OC(O)—, —NHC(O)—, —$C_6H_4$—, or a direct bond;

$R_{51}$ is —H, $C_1$-$C_6$-alkyl, $C_2$-$C_6$-alkenyl, $C_2$-$C_6$-alkynyl, halo, —$CF_3$, —$OCF_3$, —OH, —$NH_2$, mono-$C_1$-$C_6$ alkyl amino, di-$C_1$-$C_6$ alkyl amino, —SH, —$CO_2H$, —CN, —$NO_2$, —$SO_3H$, or a saturated or mono- or poly-unsaturated $C_5$-$C_{14}$-mono- or fused poly-cyclic hydrocarbyl, optionally containing one or two heteroatoms per ring, wherein $R_{51}$ is optionally substituted with one, two, or three substituents selected from the group consisting of: $C_1$-$C_6$-alkyl, halo, —$CF_3$, —$OCF_3$, —OH, —$NH_2$, mono-$C_1$-$C_6$ alkyl amino, and di-$C_1$-$C_6$ alkyl amino;

$R_{52}$ is —H, $C_1$-$C_6$-alkyl, $C_2$-$C_6$-alkenyl, $C_2$-$C_6$-alkynyl, halo, —$CF_3$, —$OCF_3$, —OH, —$NH_2$, mono-$C_1$-$C_6$ alkyl amino, di-$C_1$-$C_6$ alkyl amino, —SH, —$CO_2H$, —CN, —$NO_2$, —$SO_3H$, or a saturated or mono- or poly-unsaturated $C_5$-$C_{14}$-mono- or fused poly-cyclic hydrocarbyl, optionally containing one or two heteroatoms per ring; and wherein n is 0, 1, 2, or 3;

provided that an O or S is not singly bonded to another O or S in a chain of atoms;

the process comprising:
(i) treating a compound of formula III:

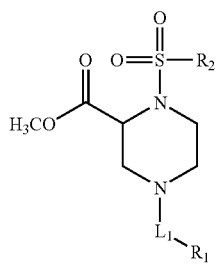

with hydroxylamine to obtain a hydroxycarbamoylpiperazine of formula IV:

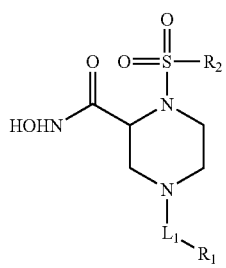

(ii) treating the hydroxycarbamoylpiperazine of formula IV with benzhydrylpiperazine to obtain a precipitate of the corresponding complex of formula V:

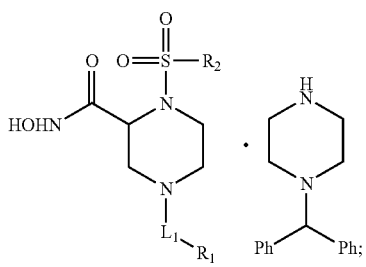

(iii) separating the precipitate from solution (e.g., by filtration or decantation), optionally washing the precipitate, and optionally removing the benzhydrylpiperazine to obtain the free acid; and (iv) treating the precipitate of the complex of formula V with base and magnesium salt to obtain the magnesium salt/complex of a compound formula I.

Part (i) of the process can be carried out at a temperature of from about 0° C. to about the 30° C., more particularly about 10° C. to about 25° C., and even more particularly 15-25° C.

Part (i) of the process can be carried out in at least one polar, aprotic solvent. Suitable, but non-limiting solvents include N,N-dimethylformamide, N,N-dimethylacetamide, N-methylpyrrolidone, tetrahydrofuran, tetramethyltetrahydrofuran, glyme, methyl t-butyl ether, dimethylsulfoxide, or mixtures thereof. One such solvent is N,N-dimethylformamide.

Part (i) of the process can employ an aqueous solution of hydroxylamine, such as 50% aqueous solution in water.

Hydroxylamine can be used in an excess from 1.001 to 100 equivalents, based on the amount of compound of formula III.

Particularly, hydroxylamine can be used in an excess from 25 to 100 equivalents, based on the amount of compound of formula III. More particularly, hydroxylamine is used in an excess from 80 to 90 equivalents, based on the amount of compound of formula III. About 85 equivalents of hydroxylamine is also suitable.

Part (i) of the process can be carried out for about 0.5 to about 24 hours. Other reaction times for part (i) are about 8 hours to about 10 hours. Yet another reaction time for part (i) is 10 hours.

Part (ii) of the process can be carried out at in least one non-polar or polar, aprotic solvent. The solvent can be a single solvent (e.g., toluene) or a mixture of two or more solvents. Suitable, non-limiting examples of solvents are isopropyl acetate, ethyl acetate, isopropyl ether, diethylether, dichloromethane, chloroform, tetrahydrofuran, acetone, toluene, acetonitrile, or mixtures thereof. One such solvent is the mixture of isopropyl acetate and diisopropyl ether.

One equivalent of benzhydrylpiperazine can be utilized for each equivalent of compound of formula IV. The reaction of part (ii) can be carried out for about 0.5 to about 4 hours. Another reaction time for part (ii) is about 0.5 hours.

Part (ii) of the process can be carried out at a temperature of from about −10° C. to about the 30° C. For example, the temperature can be between 20° C. and 30° C. In particular, the temperature can be about 25° C.

Part (iv) of the process can employ a base. Non-limiting examples of a base that can be employed include an alkali metal base, such as sodium hydroxide or potassium hydroxide. In another embodiment of part (iv), the base used is sodium hydroxide. Addition of the base can be followed by addition of one or more magnesium salts. A non-limiting example of a magnesium salt is magnesium acetate, which can be a 20% aqueous solution in water.

Part (iv) of the process can be carried out in a polar, protic solvent. Suitable, non-limiting examples of solvents are ethanol, methanol, isopropanol, n-propanol, n-butanol, formic acid, acetic acid, or mixtures thereof. In particular, the solvent is ethanol, methanol, or isopropanol. More particularly, the solvent is ethanol.

Addition of the base in part (iv) can be carried out at a temperature of from about 0° C. to about the 30° C. One such temperature is below 25° C. Addition of the magnesium salt in part (iv) can be carried out at a temperature of from about 0° C. to about the 30° C. One such temperature is below 25° C.

Part (iv) of the process can employ treatment with an acid prior to addition of the base to remove benzyhydrylpiperazine. One example of an acid is hydrochloric acid. Non-limiting examples of acids that can be used include sulfuric acid, phosphoric acid, nitric acid and perchloric acid.

Part (iv) of the process can be carried out for about 0.5 to about 3 hours. Other reaction times for part (iv) are about 0.5 hours to about 2 hours. Additional reaction time for part (iv) is about 1 hour to about 1.5 hours.

In another embodiment, this process further comprises the step of purifying the compound of formula III in part (i) by silica gel chromatography.

In another embodiment, the purification in parts (ii) and (iii) of this process are omitted, and the compound of formula III in part (i) is purified by silica gel chromatography is added.

Parts (i)-(iv) of the process can occur in sequential order.

In one embodiment of this aspect, the magnesium salt/complex of a compound of formula I has a purity of at least 99%.

In particular, the magnesium salt/complex of formula I to be prepared as discussed above is one in which, $L_1$ is —C(O)—;
$R_1$ is —OR$_{11}$,
 where $R_{11}$ is —C$_1$-C$_3$alkyl-O—C$_1$-C$_3$alkyl;
$R_2$ is —R$_{21}$-L$_2$-R$_{22}$,
 where $R_{21}$ is phenyl substituted with 1, 2 or 3 halo,
 $L_3$ is —O—, and
 $R_{22}$ is phenyl substituted with 1, 2 or 3 halo.

In a particular embodiment, the magnesium salt/complex to be prepared as discussed above is the magnesium salt/complex of 4-(4-(4-chlorophenoxy)-3,5-difluorophenylsulfonyl)-3-(hydroxycarbamoyl)piperazine-1-carboxylic acid (R)-2-methoxyethyl ester.

In an embodiment of the process discussed above, a process of preparing a magnesium salt/complex of a compound of formula VI is provided:

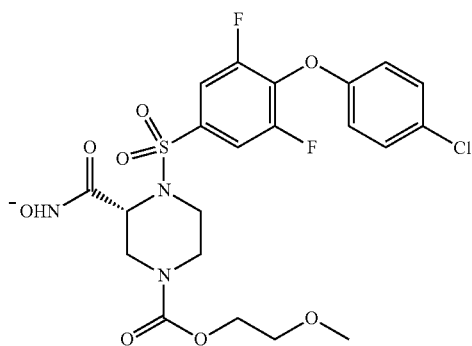

VI comprising:
(i) treating a compound of formula VII:

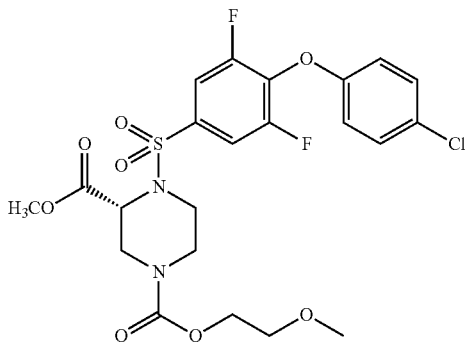

VII with hydroxylamine to obtain a hydroxycarbamoylpiperazine of formula VIII:

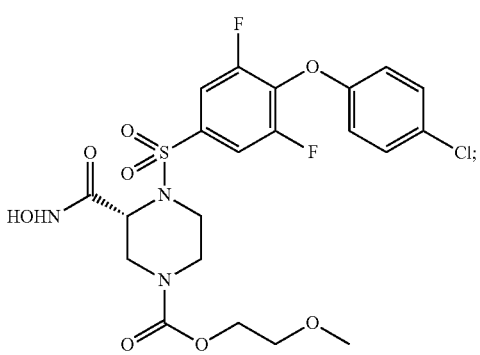

VIII (ii) treating the hydroxycarbamoylpiperazine of formula VIII with benzhydrylpiperazine to obtain a precipitate of the corresponding complex of formula IX:

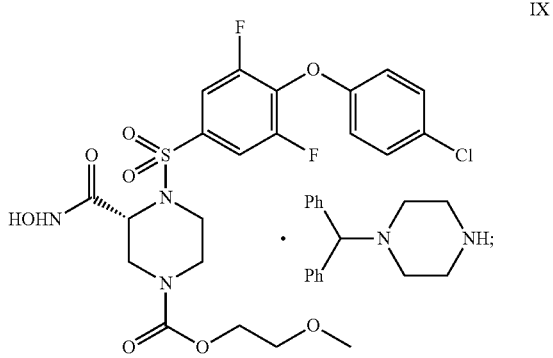

IX (iii) separating the precipitate from solution (e.g., by filtration or decantation), optionally washing the precipitate, and optionally removing the benzyhdrylpiperazine to obtain the free acid); and (iv) treating the precipitate of the complex of formula IX with base and magnesium salt to obtain the magnesium salt/complex of a compound of formula VI.

Part (i) of the process of this embodiment can be carried out at a temperature of from about 0° C. to about the 30° C. The temperature can be about 10° C. to about 25° C. In particular, the temperature can be 15-25° C.

Part (i) of the process of this embodiment is carried out in a solvent. Part (i) of the process of this embodiment can be carried out in at least one polar, aprotic solvent. Suitable, but non-limiting solvents include N,N-dimethylformamide, N,N-dimethylacetamide, N-methylpyrrolidone, tetrahydrofuran, tetramethyltetrahydrofuran, glyme, methyl t-butyl ether, dimethylsulfoxide, or mixtures thereof. One such solvent is N,N-dimethylformamide.

Part (i) of the process of this embodiment can employ an aqueous solution of hydroxylamine, such as 50% aqueous solution in water.

Hydroxylamine can be used in this embodiment in an excess from 1.001 to 100 equivalents, based on the amount of compound of formula VII. In particular, hydroxylamine can be used in an excess from 25 to 100 equivalents, based on the amount of compound of formula VII. More particularly, hydroxylamine can be used in an excess from 80 to 90 equivalents, based on the amount of compound of formula VII. Even more particularly, about 85 equivalents of hydroxylamine can be utilized.

Part (i) of the process of this embodiment can be carried out for about 0.5 to about 24 hours. Other reaction times for part (i) are about 8 hours to about 10 hours. Yet another reaction time for part (i) is 10 hours.

Part (ii) of the process of this embodiment can be carried out in at least one non-polar or polar, aprotic solvent. The solvent can be a single solvent (e.g., toluene) or a mixture of two or more solvents. Suitable, non-limiting examples of solvents are isopropyl acetate, ethyl acetate, isopropyl ether, diethylether, dichloromethane, chloroform, tetrahydrofuran, acetone, toluene, acetonitrile, or mixtures thereof. One such solvent is the mixture of isopropyl acetate and diisopropyl ether.

One equivalent of benzhydrylpiperazine can be utilized for each equivalent of compound of formula VIII. The reaction of part (ii) can be carried out for about 0.5 to about 4 hours. Another reaction time for part (ii) is about 0.5 hours.

Part (ii) of this embodiment can be carried out at a temperature of from about −10° C. to about the 30° C. For example, the temperature can be between 20° C. and 30° C. Also, the temperature can be about 25° C.

Part (iv) of the process of this embodiment employs a base. Non-limiting examples of a base that can be used include an alkali metal base, such as sodium hydroxide or potassium hydroxide. In another embodiment of part (iv), the base is sodium hydroxide. Addition of the base can be followed by addition of magnesium salt. A non-limiting example of the magnesium salt is magnesium acetate, which can be 20% aqueous solution in water.

Part (iv) of the process of this embodiment can be carried out in a polar, protic solvent. Suitable, non-limiting examples of solvents are ethanol, methanol, isopropanol, n-propanol, n-butanol, formic acid, acetic acid, or mixtures thereof. In one aspect, the solvent is ethanol, methanol, or isopropanol. In particular, the solvent can be ethanol.

Addition of the base in part (iv) of this embodiment can be carried out at a temperature of from about 0° C. to about the 30° C. One such temperature is below 25° C. Addition of the magnesium salt in part (iv) can be carried out at a temperature of from about 0° C. to about the 30° C. One such temperature is below 25° C.

Part (iv) of the process of this embodiment can employ treatment with an acid prior to addition of the base to remove benzyhydrylpiperazine. Non-limiting examples of acids that can be used include inorganic acids such as hydrochloric acid, phosphoric acid, nitric acid, sulfuric acid, and perchloric acid.

Part (iv) of the process of this embodiment can be carried out for about 0.5 to about 3 hours. Other reaction times for part (iv) are about 0.5 hours to about 2 hours. An additional reaction time for part (iv) is about 1 hour to about 1.5 hours.

In another embodiment, this process further comprises the step of purifying the compound of formula VII in part (i) by silica gel chromatography.

In another embodiment, the purification in parts (ii) and (iii) of this process are omitted, and the compound of formula VII in part (i) is purified by silica gel chromatography is added.

Parts (i)-(iv) of the process can occur in sequential order.

In one embodiment of this aspect, the magnesium salt/complex of a compound of formula VI has a purity of at least 99%, at least 99.4%, or at least 99.7%. Yields can be at least 80% or at least 85%.

In another aspect, a process of purifying and preparing a salt/complex of a compound of formula I is provided:

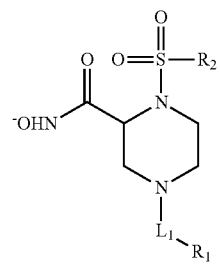

I wherein
$L_1$ is —C(O)—, —S(O)$_2$—, or —(CH$_2$)$_n$—;
$R_1$ is —H, —OR$_{11}$, —(CH$_2$)$_n$R$_{11}$, —C(O)R$_{11}$, or —NR$_{12}$R$_{13}$;

$R_{11}$, $R_{12}$, and $R_{13}$ are each independently:
a) $R_{50}$;
b) saturated or mono- or poly-unsaturated $C_5$-$C_{14}$-mono- or fused poly-cyclic hydrocarbyl, optionally containing one or two heteroatoms per ring, wherein the saturated or mono- or poly-unsaturated $C_5$-$C_{14}$-mono- or fused poly-cyclic hydrocarbyl is optionally substituted with one or two independently selected $R_{50}$ substituents;
c) $C_1$-$C_6$-alkyl, $C_2$-$C_6$-alkenyl, $C_2$-$C_6$-alkynyl, or —C(O)H, each of which is optionally substituted with one, two or three substituents independently selected from $R_{50}$ and saturated or mono- or poly-unsaturated $C_5$-$C_{14}$-mono- or fused poly-cyclic hydrocarbyl, optionally containing one or two heteroatoms per ring and optionally substituted with one, two or three independently selected $R_{50}$ substituents; or
d) $R_{12}$ and $R_{13}$ together with the N to which they are covalently bound form a $C_5$-$C_6$ heterocycle optionally containing a second heteroatom, wherein the $C_5$-$C_6$ heterocycle is optionally substituted with one or two independently selected $R_{50}$ substituents;

$R_2$ is —$R_{21}$-$L_2$-$R_{22}$;
$R_{21}$ is saturated or mono-, or poly-unsaturated $C_5$-$C_{14}$-mono- or fused poly-cyclic hydrocarbyl, optionally containing one or two heteroatoms per ring and optionally substituted with one, two, or three independently selected $R_{52}$ substituents;
$L_2$ is —O—, —C(O)—, —CH$_2$—, —NH—, —S(O)$_2$—, or a direct bond;
$R_{22}$ is saturated or mono- or poly-unsaturated $C_5$-$C_{14}$-mono- or fused poly-cyclic hydrocarbyl, optionally containing one or two heteroatoms per ring and optionally substituted with one, two, or three independently selected $R_{52}$ substituents; and $R_{50}$ is $R_{51}$-$L_3$-(CH$_2$)$_n$—;
$L_3$ is —O—, —NH—, —S(O)$_{0-2}$—, —C(O)—, —C(O)O—, —C(O)NH—, —OC(O)—, —NHC(O)—, —C$_6$H$_4$—, or a direct bond;
$R_{51}$ is —H, $C_1$-$C_6$-alkyl, $C_2$-$C_6$-alkenyl, $C_2$-$C_6$-alkynyl, halo, —CF$_3$, —OCF$_3$, —OH, —NH$_2$, mono-$C_1$-$C_6$ alkyl amino, di-$C_1$-$C_6$ alkyl amino, —SH, —CO$_2$H, —CN, —NO$_2$, —SO$_3$H, or a saturated or mono- or poly-unsaturated $C_5$-$C_{14}$-mono- or fused poly-cyclic hydrocarbyl, optionally containing one or two heteroatoms per ring, wherein $R_{51}$ is optionally substituted with one, two, or three substituents selected from the group consisting of: $C_1$-$C_6$-alkyl, halo, —CF$_3$, —OCF$_3$, —OH, —NH$_2$, mono-$C_1$-$C_6$ alkyl amino, and di-$C_1$-$C_6$ alkyl amino; and
$R_{52}$ is —H, $C_1$-$C_6$-alkyl, $C_2$-$C_6$-alkenyl, $C_2$-$C_6$-alkynyl, halo, —CF$_3$, —OCF$_3$, —OH, —NH$_2$, mono-$C_1$-$C_6$ alkyl amino, di-$C_1$-$C_6$ alkyl amino, —SH, —CO$_2$H, —CN, —NO$_2$, —SO$_3$H, or a saturated or mono- or poly-unsaturated $C_5$-$C_{14}$-mono- or fused poly-cyclic hydrocarbyl, optionally containing one or two annular heteroatoms per ring; and
wherein n is 0, 1, 2, or 3;
provided that an O or S is not singly bonded to another O or S in a chain of atoms; comprising:
(i) treating the compound of formula I with benzhydrylpiperazine to obtain a precipitate of the corresponding complex

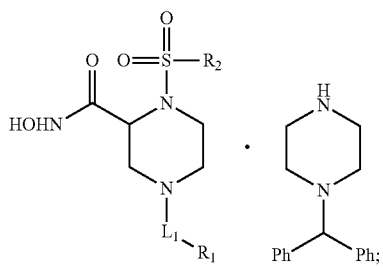

(ii) separating the precipitate from solution (e.g., by filtration or decantation), optionally washing the precipitate, and optionally removing the benzyhdrylpiperazine to obtain the free acid; and (iii) treating the precipitate of the complex with base and a salt to yield a salt/complex of the compound.

Part (i) of the purification can be carried out in at least one non-polar or polar, aprotic solvent. Further, part (i) of the process can be carried out in a mixture of two or more solvents. Suitable, non-limiting examples of solvents are isopropyl acetate, ethyl acetate, isopropyl ether, diethylether, dichloromethane, chloroform, tetrahydrofuran, acetone, toluene, acetonitrile, or mixtures thereof. One such solvent is the mixture of isopropyl acetate and disopropyl ether.

One equivalent of benzhydrylpiperazine can be utilized for each equivalent of the compound of formula I. Part (i) of the process can be carried out for about 0.5 to about 4 hours. The reaction time for part (i) can be about 0.5 hours.

Part (i) can be carried out at a temperature of from about −10° C. to about the 30° C. For example, the temperature can be between 20° C. and 30° C. Also, the temperature can be about 25° C.

Part (iii) of this aspect can employ a base. Non-limiting examples of a base that can be used include an alkali metal base, such as sodium hydroxide or potassium hydroxide. In another embodiment of part (iv), the base is sodium hydroxide. Addition of the base can be followed by addition of magnesium salt. A non-limiting example of the magnesium salt is magnesium acetate, which can be 20% aqueous solution in water.

Part (iii) of this aspect can be carried out in a polar, protic solvent. Suitable, but non-limiting solvents include ethanol, methanol, isopropanol, n-propanol, n-butanol, formic acid, acetic acid, or mixtures thereof. In particular, the solvent is ethanol, methanol, or isopropanol. More particularly, the solvent is ethanol.

Addition of the base in part (iii) can be carried out at a temperature of from about 0° C. to about the 30° C. One such temperature is below 25° C. Addition of the magnesium salt in part (iii) can be carried out at a temperature of from about 0° C. to about the 30° C. One such temperature is below 25° C.

Part (iii) of the process can employ treatment with an acid prior to addition of the base to remove benzyhdryl piperazine. Non-limiting examples of acids that can be used include inorganic acids such as hydrochloric acid, phosphoric acid, nitric acid, sulfuric acid, and perchloric acid.

Part (iii) of this aspect can be carried out for about 0.5 to about 3 hours. Another reaction time for part (iii) is about 0.5 hours to about 2 hours. Yet another reaction time for part (iii) is about 1 hour to about 1.5 hours.

Parts (i)-(iii) of the process can occur in sequential order.

In one embodiment of this aspect, the salt/complex of a compound of formula I has a purity of at least 99%.

In one embodiment of this aspect, in the salt/complex of the compound of formula I, $L_1$ is —C(O)—;

$R_1$ is —$OR_{11}$, where $R_{11}$ is —$C_1$-$C_3$ alkyl-O—$C_1$-$C_3$alkyl;

$R_2$ is —$R_{21}$-$L_2$-$R_{22}$, where $R_{21}$ is phenyl substituted with 1, 2 or 3 halo, $L_3$ is —O—, and $R_{22}$ is phenyl substituted with 1, 2 or 3 halo.

In a particular embodiment of this aspect, a process for purifying and preparing a salt/complex of 4-(4-(4-chlorophenoxy)-3,5-difluorophenylsulfonyl)-3-(hydroxycarbamoyl)piperazine-1-carboxylic acid (R)-2-methoxyethyl ester is provided.

If any of the additives are added, one skilled in the art will recognize the appropriate amount of the additive that should be added. The use of such reagents is known in the art of organic synthesis and medicinal chemistry.

Also provided are compositions comprising a therapeutically effective amount of magnesium salt/complex of compound of formula I and at least one pharmaceutically acceptable carrier, solvent, adjuvant or diluent.

In another aspect, further provided are methods of treating disease such as cancer, arthritis, diseases related to angiogenesis, such as renal diseases, heart diseases, such as heart failure, atherosclerosis, and stroke, inflammation, ulcer, infertility, scleroderma, endometriosis, mesothelioma, and diabetes. In addition, methods of treating forms of cancer, and arthritis in a patient in need of such treatment, comprising administering to a patient in need of such treatment an effective amount of magnesium salt/complex of a compound of formula I are encompassed. In another embodiment, the diseases that can be treated by administering to a patient in need of such treatment an effective amount of magnesium salt/complex of a compound of formula I include breast cancer, arthritis, renal disease, heart disease, stroke or inflammation.

Heart disease is linked to to JAG1 mutations, implying that ADAM-10 can potentially have a role in treating this type of disorder. See Eldadah, Z. A., A. Hamosh, et al. (2001). "Familial Tetralogy of Fallot caused by mutation in the jagged1 gene." *Hum Mol Genet* 10(2): 163-9. See also Loomes, K. M., L. A. Underkoffler, et al. (1999). "The expression of Jagged1 in the developing mammalian heart correlates with cardiovascular disease in Alagille syndrome." *Hum Mol Genet* 8(13): 2443-9.

Stroke is linked to Notch-3 mutations, implying that ADAM-10 can potentially have a role in treating this type of disorder. See Escary, J. L., M. Cecillon, et al. (2000). "Evaluation of DHPLC analysis in mutational scanning of Notch3, a gene with a high G-C content." *Hum Mutat* 16(6): 518-26. See also Fryxell, K. J., M. Soderlund, et al. (2001). "An animal model for the molecular genetics of CADASIL. (Cerebral autosomal dominant arteriopathy with subcortical infarcts and leukoencephalopathy)." *Stroke* 32(1): 6-11.

In another aspect, also provided are methods of treating a subject suffering for disease or disorder in which ADAM-10 plays a critical role, the method comprising administering to a patient in need of such treatment an effective amount of magnesium salt/complex of compound of formula I.

In another aspect, further provided is a magnesium salt/complex of compound of formula I, preferably as a composition, in a kit with instructions for contents to treat a disease or disorder. A packaged pharmaceutical composition comprising compound of magnesium salt/complex of compound of formula I in a container with instructions on how to use the compound is also encompassed.

In another aspect, combination therapy employing magnesium salt/complex of compound of formula I is provided. In such therapy, magnesium salt/complex of compound of formula I can be combined with other drugs or therapies known to be effective to treat the disease or disorder to enhance overall effectiveness of therapy.

In one aspect, methods for the treatment of cancer in a subject in need of such treatment comprising administering an amount of magnesium salt/complex of compound of formula I, in combination with at least one other therapeutic agent are encompassed.

In another aspect, methods for treating cancer in a subject in need of such treatment, the methods comprising administering an amount of magnesium salt/complex of compound of formula I, in combination with at least one other anti-cancer agent are encompassed.

The nature of the association between the magnesium and compound of formula I has not been determined. It is unknown whether the compounds of formula I together with the magnesium ion form a true ionic salt or a coordination complex, or whether the association between the magnesium ion and compound of formula I is partially ionic (salt) and partially coordinate covalent in character. Accordingly, we describe the composition disclosed herein as a "salt/complex," which is meant to encompass the species where the bond between the salt and the compound of formula I is ionic, covalent, and/or has characteristics of both ionic and covalent bonds. And, therefore, for the purposes of the present disclosure and claims, the following depiction of the compound of formula II:

In a further aspect, methods for treating cancer, the methods comprising administering an amount of magnesium salt/complex of compound of formula I, in combination with radiation therapy are also encompassed.

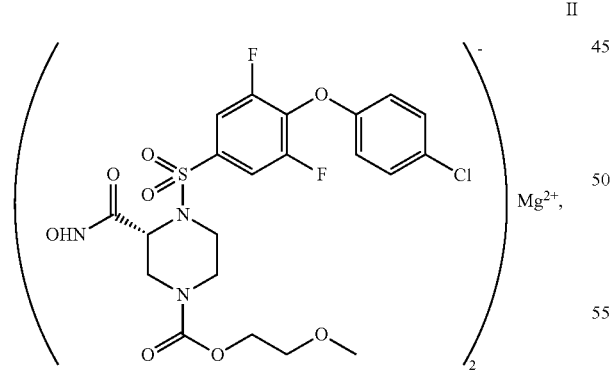

although drawn in a manner conventionally used for a true salt, does not imply anything regarding the nature of the association of the magnesium ion and the compound for formula I; as described above, that association may be ionic, coordinate covalent, or partially ionic and coordinate covalent.

The following exemplary, non-limiting compounds are intended to be within the scope of general formula I:

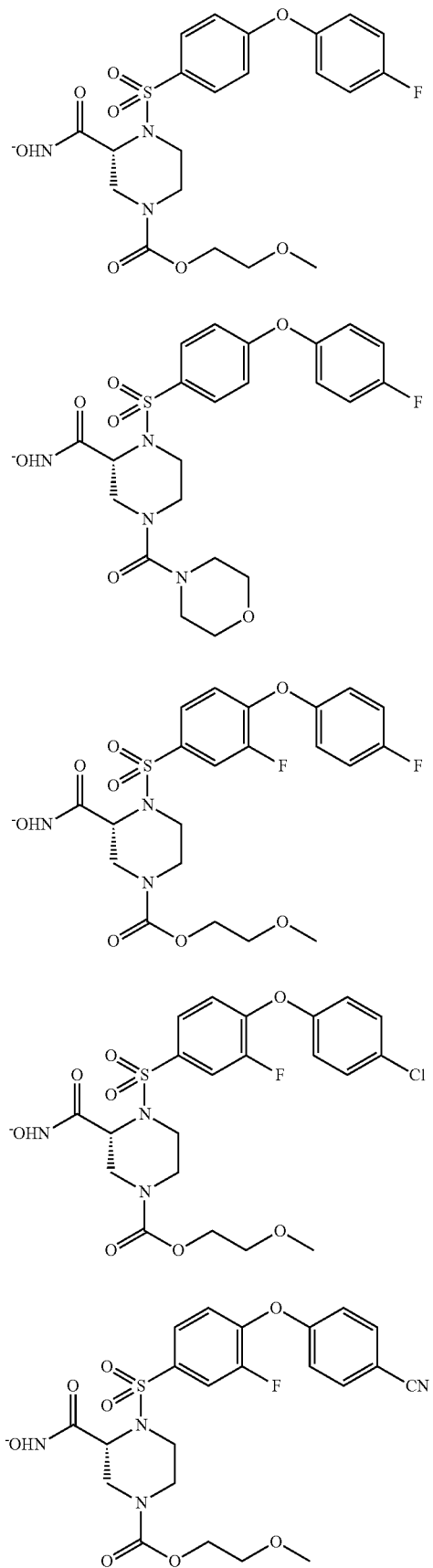

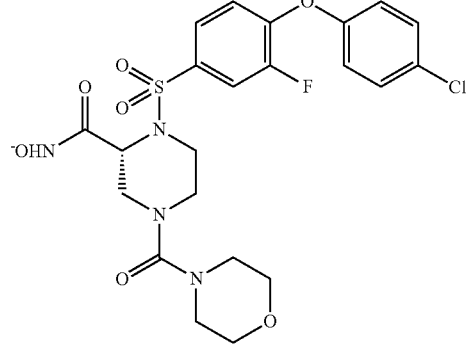
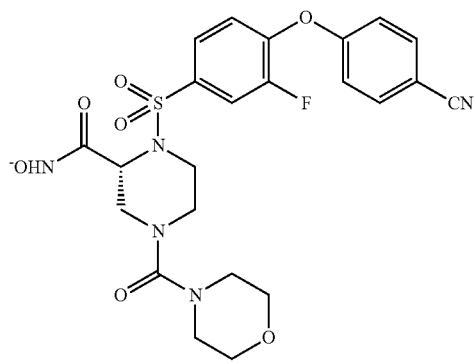
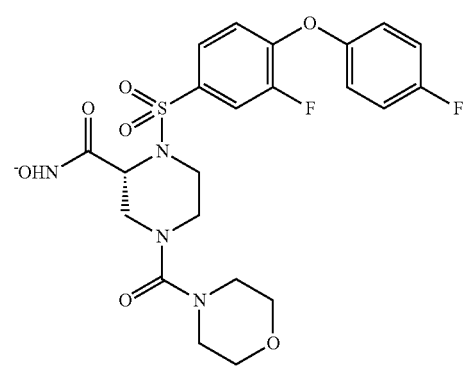
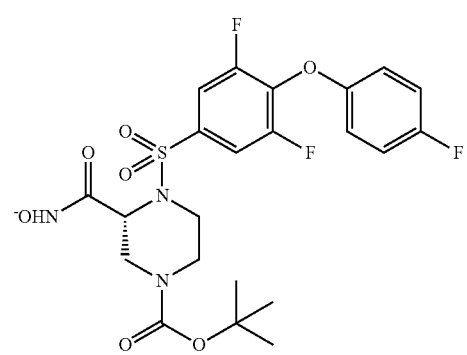
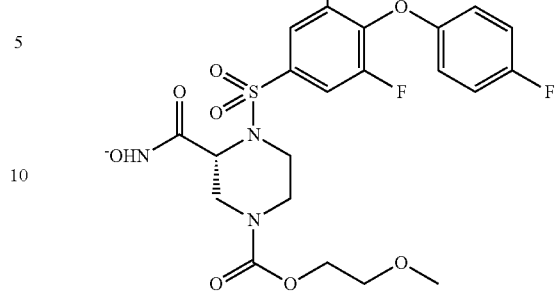
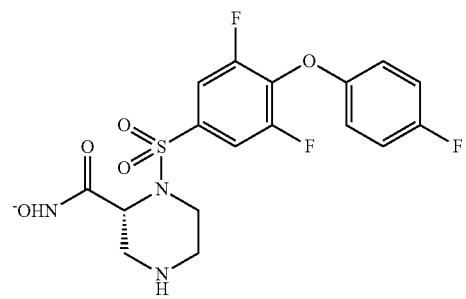
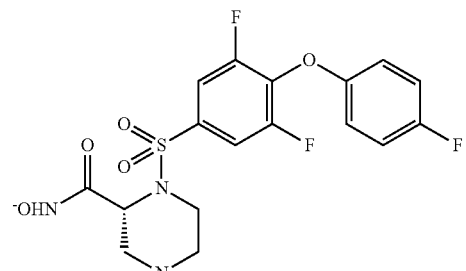
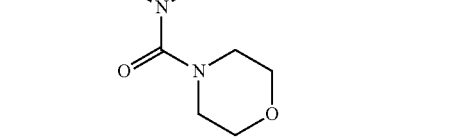
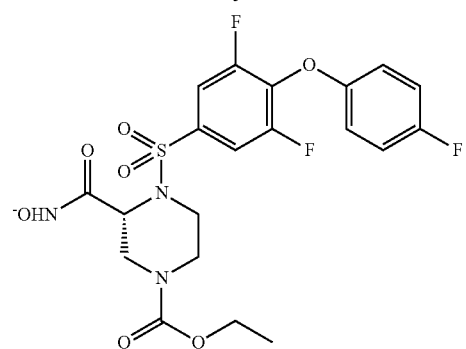
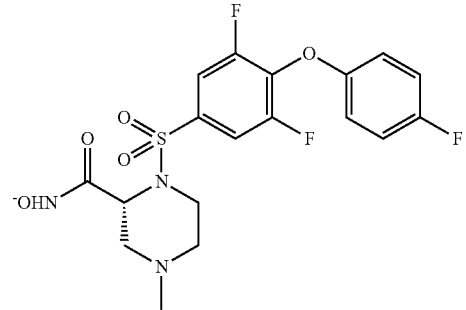

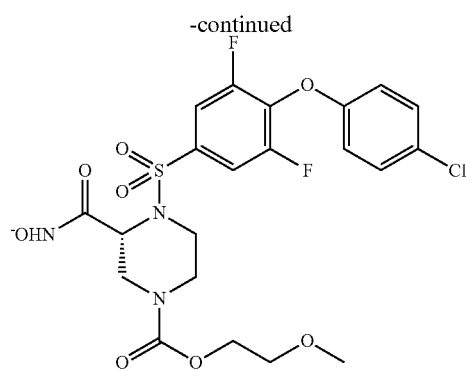
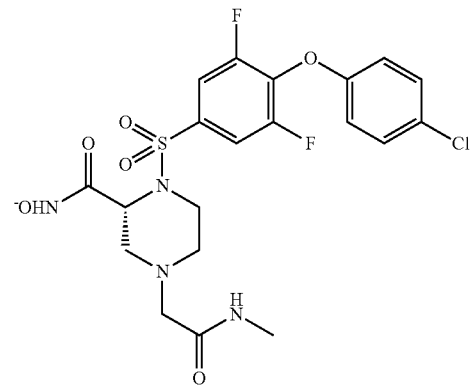
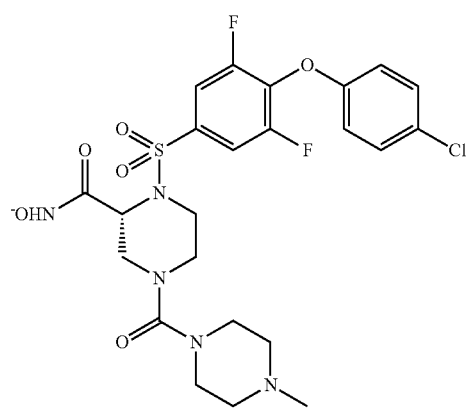
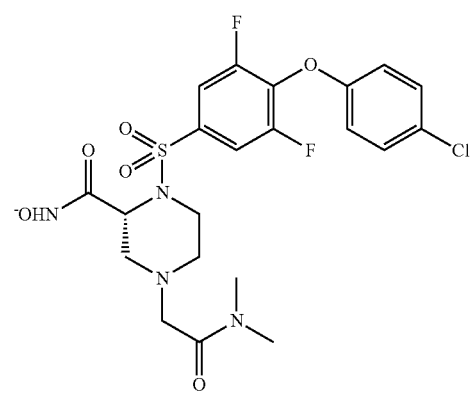
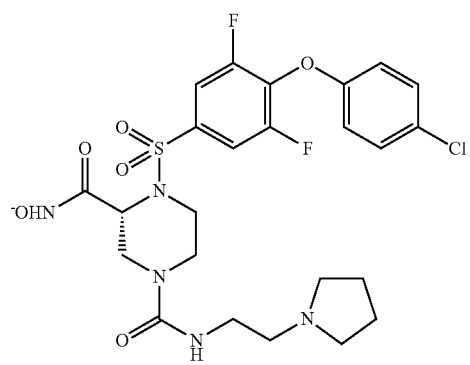
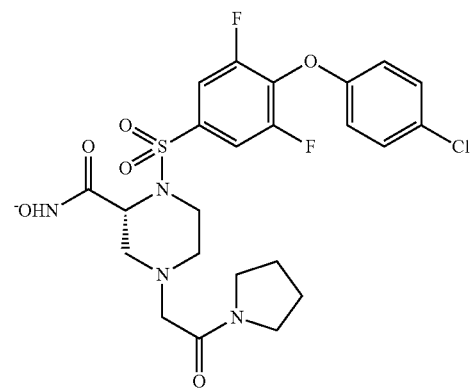
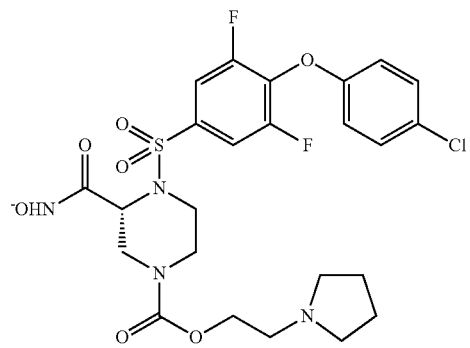
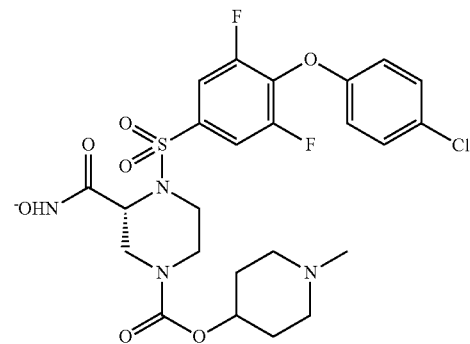

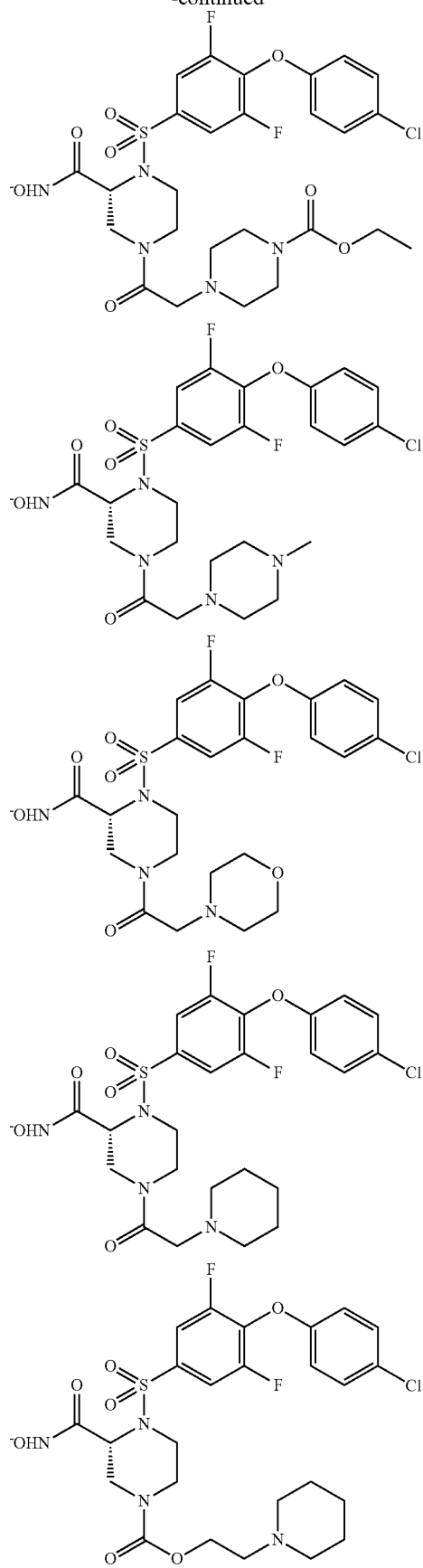
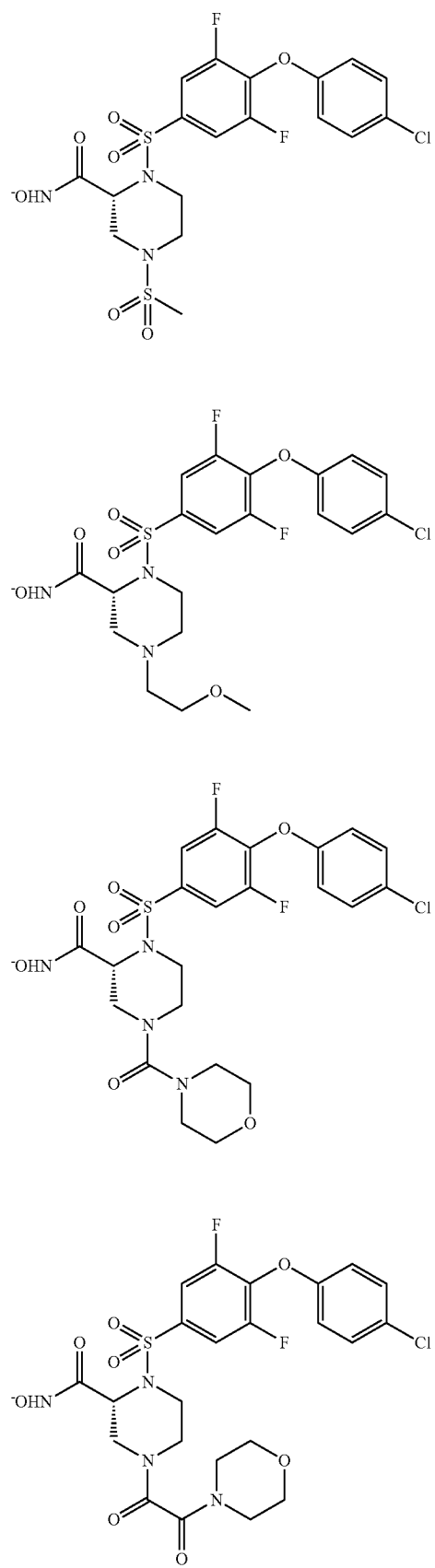

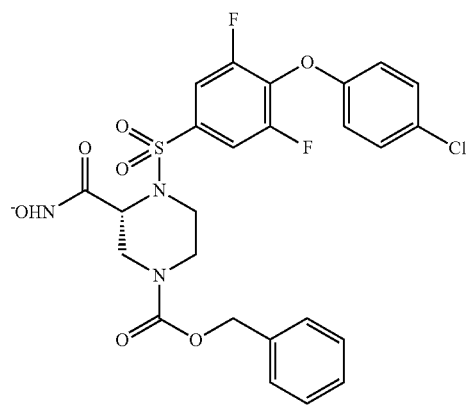
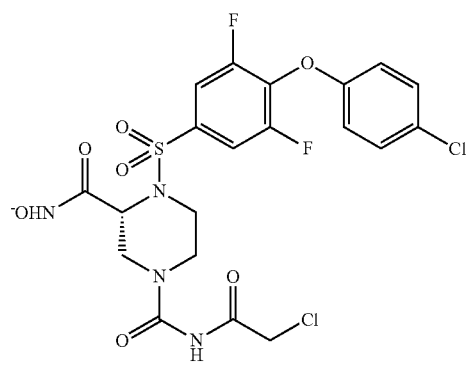
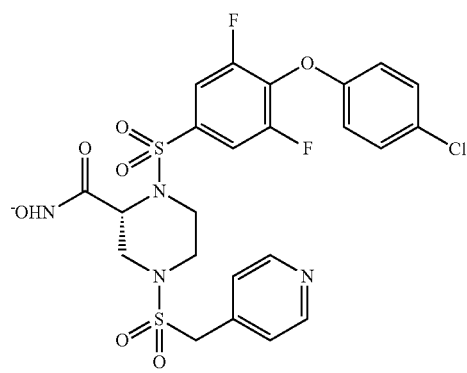
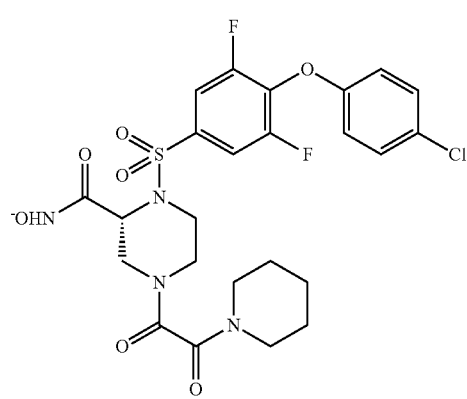
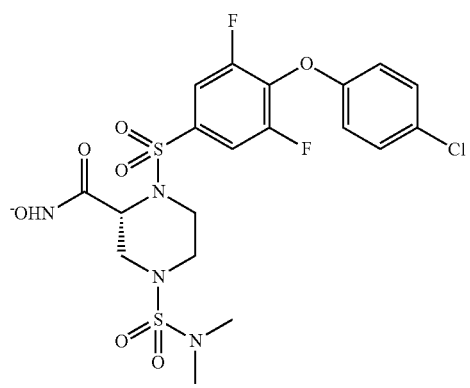
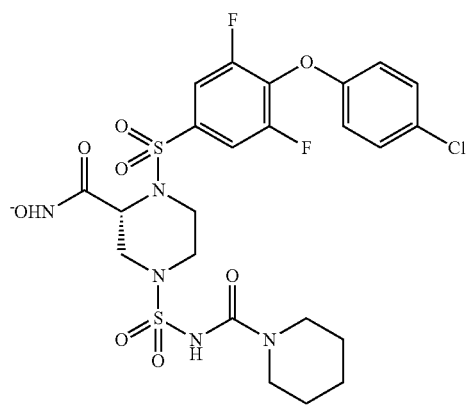
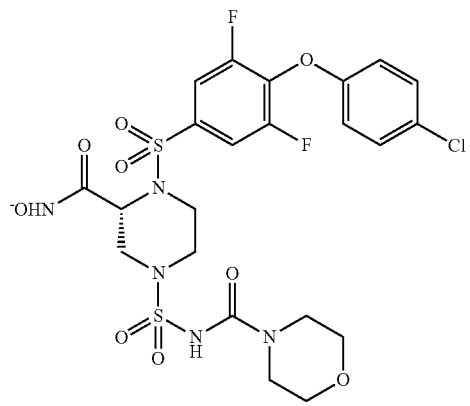
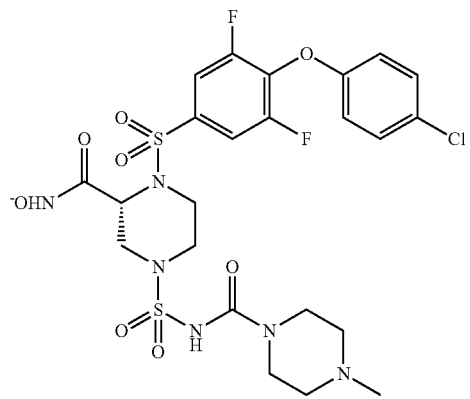

25
-continued
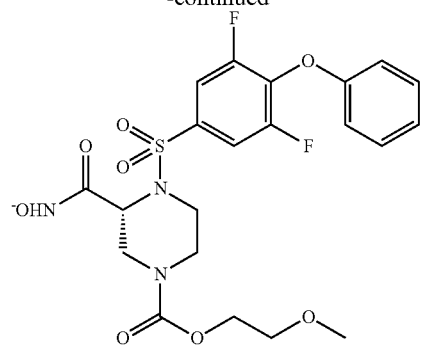
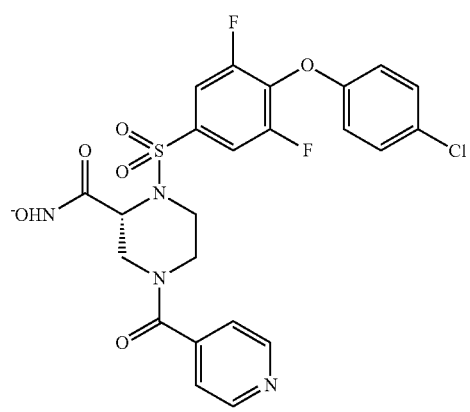
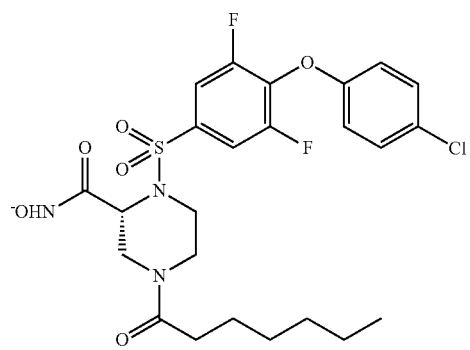
26
-continued
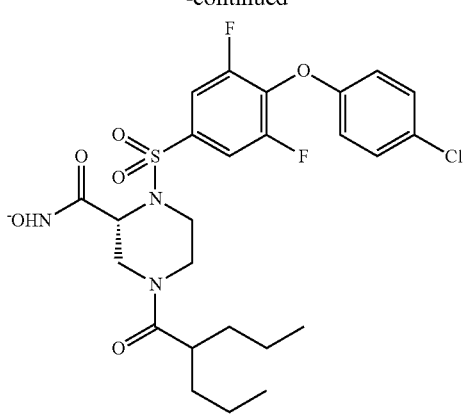
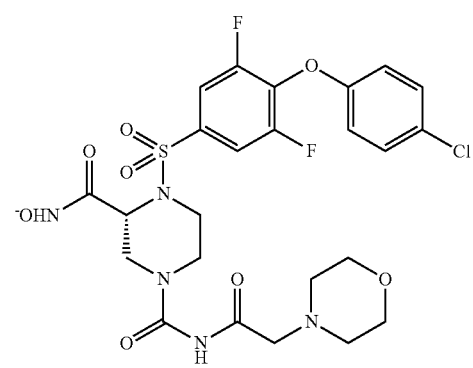
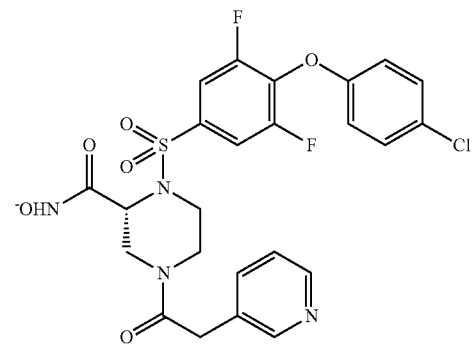

-continued
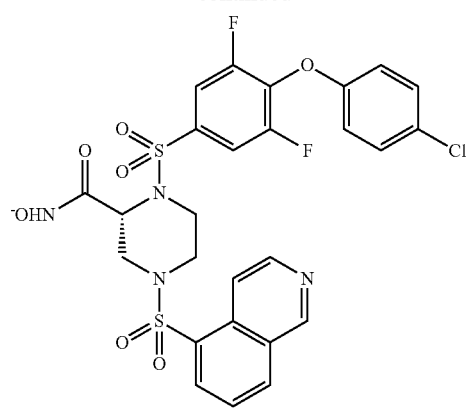
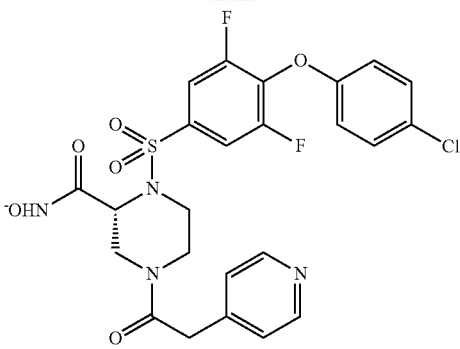
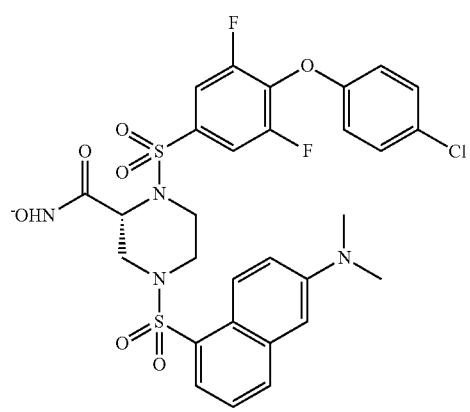
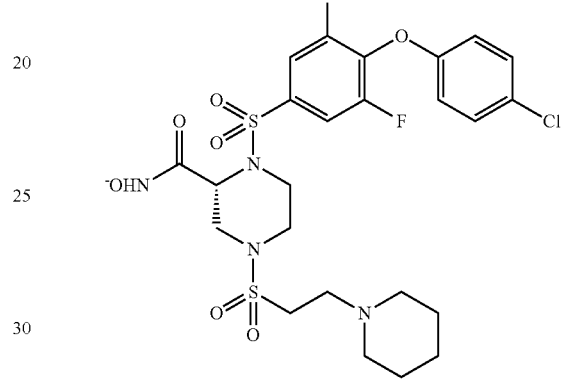
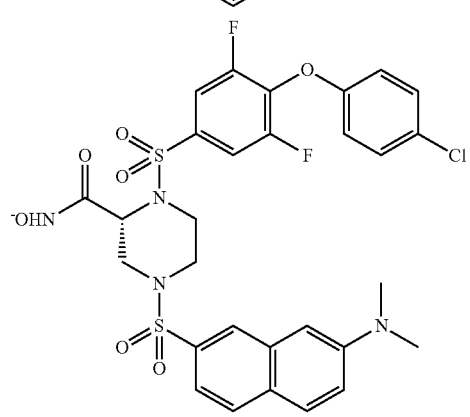
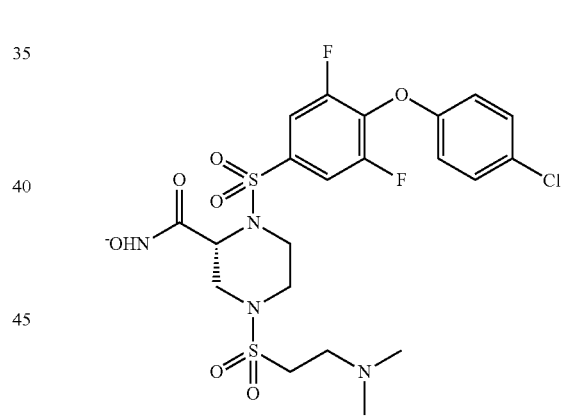
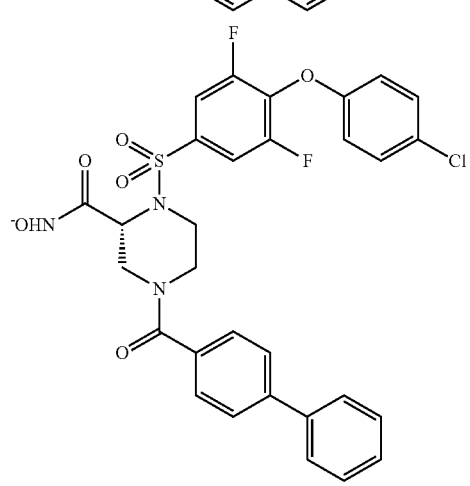
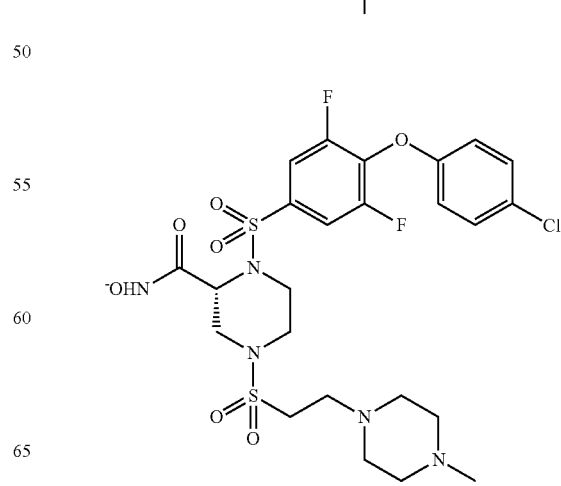

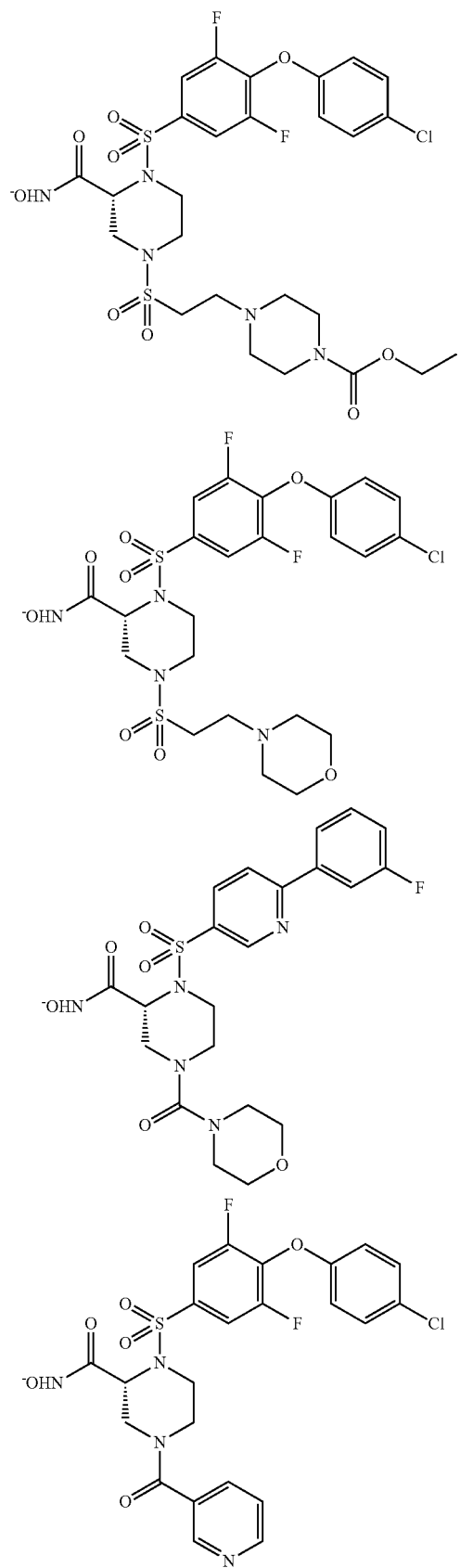
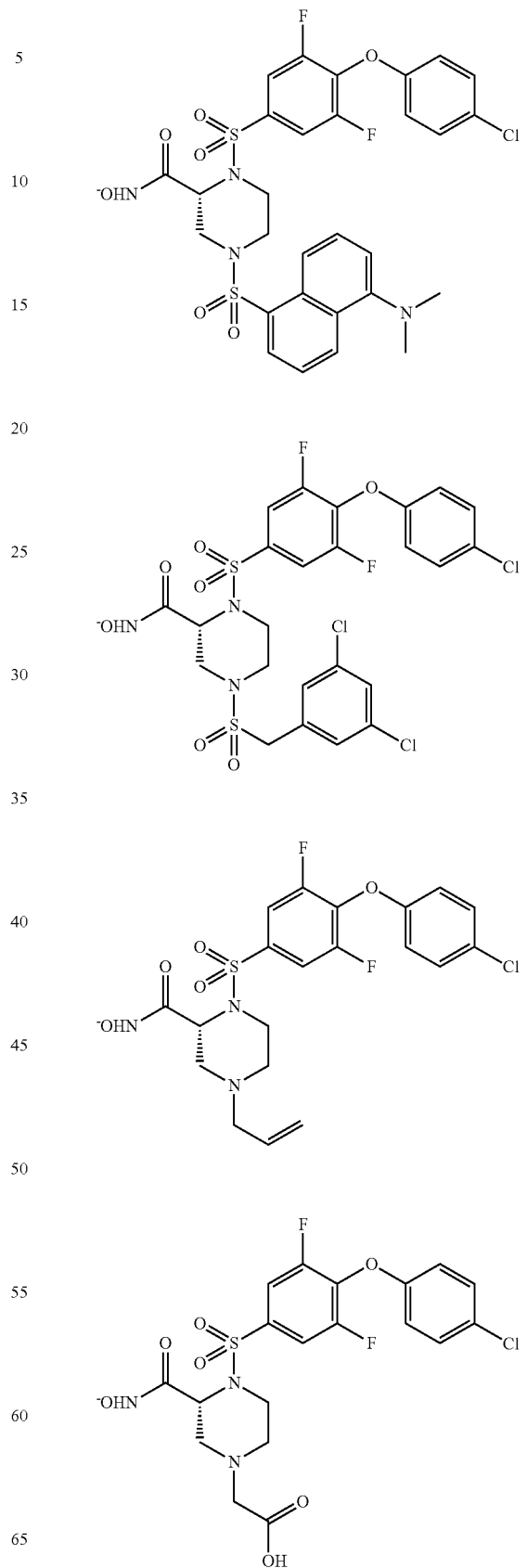

-continued

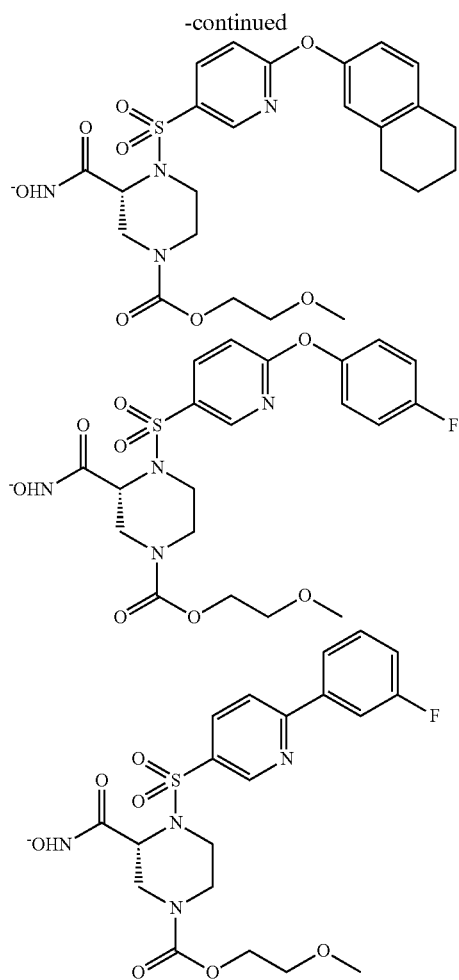

The above compounds are disclosed in WO03/106381, the disclosure of which is incorporated herein by reference in its entirety.

Hydroxycarbamoylpiperazine of formula VIII was observed to have poor stability in solution. Although the chromatographic purification of this compound produced excellent material on the small scale, large scale column chromatography failed to provide a sufficiently pure hydroxycarbamoylpiperazine of formula VIII. In particular, lengthy times required for elution of columns and evaporation of solvent on the pilot scale resulted in degradation of the compound. The purity of hydroxycarbamoylpiperazine of formula VIII obtained after part (i) ranged from 84% to 92%. The observed yields were between 63% and 78%. This hydroxycarbamoylpiperazine was of insufficient purity to produce pure magnesium salt/complex of formula VI suitable for pharmaceutical use. The direct conversion of hydroxycarbamoylpiperazine of formula VIII to the magnesium salt/complex of formula VI by omitting parts (ii) and (iii) yielded the magnesium salt/complex with the purity ranging from 96% to 97%. We discovered that this problem could be solved by first obtaining and separating a benzhydrylpiperazine complex of formula IX prior to the conversion to the magnesium salt/complex of formula IV. Yields for the process that included parts (i)-(iv) ranged from 81% to 86%. The purity of the magnesium salt/complex of formula IV was at least 99%; specifically, between 99.4% and 99.7%.

It is expected that these purities can be achieved after purification of other compounds and salts/complexes disclosed herein. That is, all processes described produce compound having a purity of at least 99%, at least 99.4%, or at least 99.7%. Yields of at least 80% or at least 85% can be obtained.

Definitions

The following paragraphs provide definitions of the various chemical moieties that make up the compounds of the disclosure and are intended to apply uniformly throughout the specification and claims unless expressly stated otherwise.

The term alkyl refers inclusively to a univalent $C_1$ to $C_{20}$ (unless explicitly stated otherwise) saturated straight, branched, cyclic, and combinations thereof alkane moiety and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. In certain instances, specific cycloalkyls are defined (e.g. $C_3$-$C_8$ cycloalkyl) to differentiate them from generically described alkyls (that, again, are intended to construe inclusion of cycloalkyls). Thus "alkyl" includes, e.g., $C_3$-$C_8$ cycloalkyl. The term "alkyl" also includes, e.g., $C_3$-$C_8$ cycloalkyl $C_1$-$C_6$ alkyl, which is a $C_1$-$C_6$ alkyl having a $C_3$-$C_8$ cycloalkyl terminus. Alkyls can be optionally substituted with any appropriate group, including but not limited to one or more moieties selected from halo, hydroxyl, amino, arylalkyl, heteroarylalkyl, alkylamino, arylamino, alkoxy, aryloxy, nitro, cyano, sulfonic acid, sulfate, phosphonic acid, phosphate, or phosphonate, either unprotected, or protected as necessary, as known to those skilled in the art or as taught, for example, in Greene, et. al., "Protective Groups in Organic Synthesis," John Wiley and Sons, Second Edition. 1991.

The term alkenyl refers to a univalent $C_2$-$C_6$ straight, branched, or in the case of $C_{5-8}$, cyclic hydrocarbon with at least one double bond.

The term aryl refers to a univalent phenyl, biphenyl, napthyl, and the like. The aryl group can be optionally substituted with any suitable group, including but not limited to one or more moieties selected from halo, hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991). As well, substitution on an aryl can include fused rings such as in tetrahydronaphthalene, chromen-2-one, dibenzofuran, and the like. In such cases, e.g. tetrahydronaphthalene, the aryl portion of the tetrahydronaphthalene is attached to the portion of a molecule described as having an aryl group.

The term hydrocarbyl refers to a hydrocarbon residue, generally. The term hydrocarbyl can be modified to mean more specific structures, for example "a saturated or mono-or poly-unsaturated $C_5$-$C_{14}$ mono-or fused-polycyclic hydrocarbyl optionally containing one, two, or three heteroatoms per ring" means a monocyclic (single) or polycyclic (for example a bridged or fused bicyclic) ring system, having between three and fourteen-ring atoms, that contains only carbon ring atoms, but optionally can contain up to three heteroatoms per ring and/or unsaturation. In this application, fused-polycyclics and fused ring systems are not necessarily all aromatic ring systems. Typically, but not necessarily, fused-polycyclics share a vicinal set of atoms, for example naphthalene or 1,2,3,4-tetrahydro-naphthalene. A spiro ring system is not a fused-polycyclic by this definition, but fused polycyclic ring systems of the disclosure may themselves have spiro rings attached thereto via a single ring atom of the fused-polycyclic.

The term heteroatom means O, S, P, or N.

The term heterocycle refers to a cyclic alkyl, alkenyl, or aryl moiety as defined above wherein one or more ring carbon atoms is replaced with a heteroatom.

The term heteroaryl specifically refers to an aryl that includes at least one of sulfur, oxygen, or nitrogen in the aromatic ring. Non-limiting examples are pyryl, furyl, pyridyl, 1,2,4-thiadiazolyl, pyrimidyl, thienyl, isothiazolyl, imidazolyl, tetrazolyl, pyrazinyl, pyrimidyl, quinolyl, isoquinolyl, benzothienyl, isobenzofuryl, pyrazolyl, indolyl, purinyl, carbazolyl, benzimidazolyl, and isoxazolyl.

The term halo refers to chloro, fluoro, iodo, or bromo.

In some examples, as will be appreciated by those skilled in the art, two adjacent carbon containing groups on an aromatic system may be fused together to form a ring structure. The fused ring structure may contain heteroatoms and may be substituted with one or more substitution groups "R". It should additionally be noted that for cycloalkyl (i.e. saturated ring structures), each positional carbon may contain two substitution groups, e.g. R and R'.

Some of the compounds of the disclosure may have imino, amino, oxo or hydroxy substituents off aromatic heterocyclic ring systems. For purposes of this disclosure, it is understood that such imino, amino, oxo or hydroxy substituents may exist in their corresponding tautomeric form, i.e., amino, imino, hydroxy or oxo, respectively.

Compounds of the disclosure are generally named using ChemDraw Ultra 10.0 (available from CambridgeSoft Corporation of Cambridge, Mass., USA) or ACD/Name (available from Advanced Chemistry Development, Inc. of Toronto, Canada). This software derives names from chemical structures according to systematic application of the nomenclature rules agreed upon by the International Union of Pure and Applied Chemistry (IUPAC), International Union of Biochemistry and Molecular Biology (IUBMB), and the Chemical Abstracts Service (CAS).

The compounds of the disclosure may have asymmetric carbon atoms, oxidized sulfur atoms or quaternized nitrogen atoms in their structure, or they may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this disclosure.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. When desired, the R- and S-isomers may be resolved by methods known to one skilled in the art, for example by: formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further part may be required to liberate the desired enantiomeric form. Alternatively, specific enantiomer may be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer may be further enriched (with concomitant loss in yield) by recrystallization.

"Optional" or "optionally" means that the subsequently described event or circumstance may or may not occur, and that the description includes instances where said event or circumstance occurs and instances in which it does not. It will be understood by one skilled in the art with respect to any group containing one or more substituents that such groups are not intended to introduce any substitution or substitution patterns that are sterically impractical and/or synthetically non-feasible. "Optionally substituted" refers to all subsequent modifiers in a term, for example in the term "optionally substituted $C_{1-8}$alkylaryl," optional substitution may occur on both the "$C_{1-8}$alkyl" portion and the "aryl" portion of the molecule.

"Substituted" alkyl, aryl, and heterocyclyl, for example, refer respectively to alkyl, aryl, and heterocyclyl, wherein one or more (for example up to about 5, in another example, up to about 3) hydrogen atoms are replaced by a substituent independently selected from, but not limited to: alkyl, halo substituted alkyl (e.g., fluoromethyl) alkoxy, alkylenedioxy (e.g. methylenedioxy), amino, $C_{1-3}$alkylamino and di-$C_{1-3}$alkylamino, amidino, aryl (e.g., phenyl), arylalkyl (e.g., benzyl), aryloxy (e.g., phenoxy), arylalkyloxy (e.g., benzyloxy), carboxy (—COOH), acyloxy, carboxamido, aminocarbonyl, benzyloxycarbonylamino (CBZ-amino), cyano, carbonyl, halogen, hydroxy, heterocyclylalkyl, heterocyclyl, nitro, sulfanyl, sulfinyl, sulfonyl, and thio.

In addition, the compounds of the present disclosure can exist in unsolvated as well as solvated forms with pharmaceutically acceptable solvents such as water, ethanol, and the like. In general, the solvated forms are considered equivalent to the unsolvated forms for the purposes of the present disclosure.

In addition, it is intended that compounds made either using standard organic synthetic techniques, including combinatorial chemistry or by biological methods, such as bacterial digestion, metabolism, enzymatic conversion, and the like are covered.

Pharmaceutical Compositions

Magnesium salt/complex of compound of formula I thereof may be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a formulation comprising magnesium salt/complex of compound of formula I and a pharmaceutically acceptable carrier. Magnesium salt/complex of compound of formula I may be present in association with one or more non-toxic pharmaceutically acceptable carriers and/or diluents and/or adjuvants, and if desired other active ingredients. The compositions containing magnesium salt/complex of compound of formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known in the art for the manufacture of pharmaceutical compositions and such compositions may contain one or more agents selected from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the disclosure may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

Magnesium salt/complex of compound of formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

The active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs. Magnesium salt/complex of compound of formula I can also be administered by a transdermal device. Preferably topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this disclosure may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present disclosure include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. Magnesium salt/complex of compound of formula I may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.1 mg to about 140 mg per kilogram of body weight per day are useful in the treatment of the above-indicated conditions (about 0.5 mg to about 7000 mg per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient, preferably 10-250 mg, and more preferably 25-250 mg. The daily dose can be administered in one to four doses per day. In the case of skin conditions, it may be preferable to apply a topical preparation of compounds of this disclosure to the affected area two to four times a day.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

Magnesium salt/complex of compound of formula I may be administered alone or in combination with at least one additional therapeutic agent or therapy, e.g., radiation therapy, to a patient in need of such treatment. The additional therapeutic agent or therapy may be administered at the same time, separately, or sequentially with respect to the administration of a compound of the disclosure. Such additional therapeutic agents included, but are not limited to, anti-cancer agents, anti-inflammatory agents, and the like.

EXAMPLES

Example 1

1-[4-(4-chlorophenoxy)-3,5-difluoro-benzenesulfonyl]-piperazine-2,4-(R)-dicarboxylic acid, 4-(2-methoxy-ethyl)-2-methyl ester (6)

Part 1—Preparation of (R)-piperazine-2-carboxylic acid bis[(R)-2-camphorsulfonic acid] salt (1)

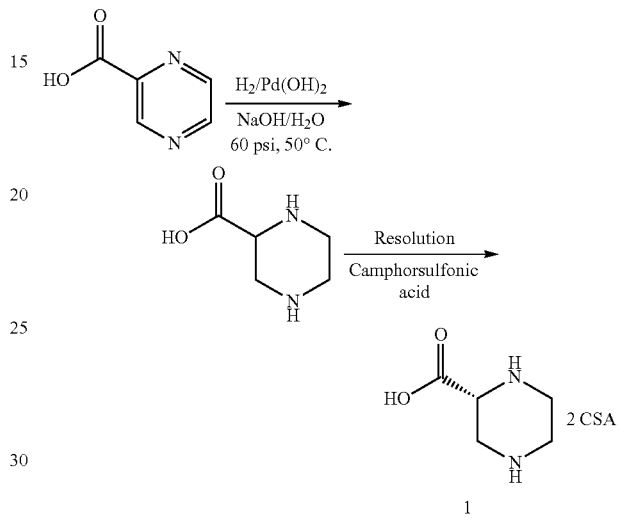

A mixture of 400 kg of water, NaOH (23.7 kg; 592.5 mol), 2-pyrazine carboxylic acid (67 kg; 540.3 mol) and 14.4 kg of 20% $Pd(OH)_2$ is purged with nitrogen and pressurized to 60 psi of hydrogen at 50° C., and maintained at that pressure and temperature for 24 h during which time seven cylinders of hydrogen are consumed. In-process analysis by TLC indicates no starting material. The reaction is filtered through Celite to remove the catalyst, and the filter is washed with 40 kg of water. The filtrate is brought to pH ~5.5 by addition of conc. HCl. R-2-camphorsulfonic acid (290 kg; 1250 mol) is added followed by 40 kg of water, and the mixture is allowed to cool to room temperature over 24 h. Precipitated product is collected by filtration, washed with ethanol and dried to yield 53.2 kg (89.5 mol; 16.5% yield) of 1 as a colorless crystalline solid (100% ee).

Part 2

Preparation of Piperazine-1,2,4-(R)-tricarboxylic acid, 1,4-di-tert-butyl ester (2)

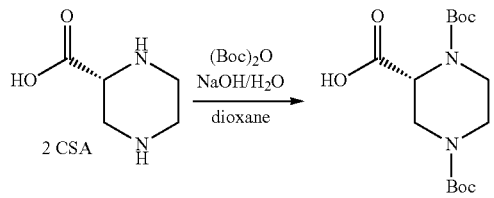

A solution of (R)-piperazine-2-carboxylic acid bis[(R)-2-camphorsulfonic acid] salt (1, 5.0 kg; 8.45 mol) in 1,4-dioxane (42.0 L) is added to a chilled (15-25° C.) solution of 6 N aqueous NaOH (5.0 L; 30 mol) at a rate such that the temperature does not exceed 25° C. When the addition is complete, the biphasic mixture is agitated at 5-15° C. for about 30 minutes. Di-tert-butyl dicarbonate (8.0 kg; 36.7 mol) is then charged while maintaining the reaction temperature of 15-20° C. When the addition is complete, the mixture is allowed to warm to 20-25° C. and is agitated at that temperature for a minimum of 16 hours. After 16 hours, the mixture is monitored by TLC for completeness of reaction (sampling every 1 to 3 hours). When the reaction is complete, the product mixture is cooled to 15-20° C., water (30.0 L) is added while maintaining the temperature at 15-20° C., and the pH of the product mixture is adjusted to 8-9 using aqueous NaOH (6 N, 2.0 L). The reaction mixture is charged with methyl-t-butyl ether (MTBE; 15.0 L). The resulting biphasic mixture is agitated at ambient temperature for about 15 minutes, and the layers are allowed to separate. The bottom, aqueous layer is removed and extracted again with MTBE (15.0 L). The organic extracts are discarded. The pH of the aqueous phase is adjusted to 4-5 using concentrated HCl (37%, 2.0 L) while maintaining the temperature of the mixture at 15-25° C. The product mixture is extracted twice with MTBE (18.0 L each). The combined MTBE extracts of the acidic aqueous layer are washed sequentially with water (8.0 L, twice) and brine (5.0 L). The organic phase is dried over MgSO₄ and filtered. The organic solvents are removed by distillation at about 35° C. under vacuum to afford a solid residue. The solid is dried under vacuum in a tray dryer at ambient temperature until a constant weight is obtained, to afford piperazine-1,2,4-(R)-tricarboxylic acid 1,4-di-tert-butyl ester (2, 3.0 kg, contains MTBE; 80% yield, corrected for residual solvent), as a waxy solid.

Part 3

Preparation of Piperazine-1,2,4-(R)-tricarboxylic acid, 1,4-di-tert-butyl-2-methyl ester (3)

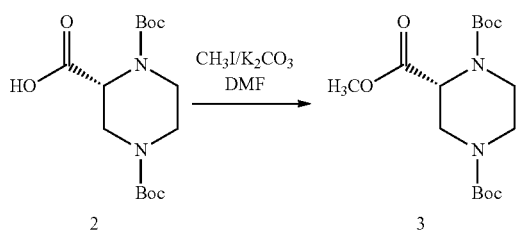 [SMILES: CC(C)(C)OC(=O)N1CCN(C(=O)OC(C)(C)C)[C@@H](C(=O)O)C1 ; COC(=O)[C@H]1CN(C(=O)OC(C)(C)C)CCN1C(=O)OC(C)(C)C]

Potassium carbonate (4.0 kg; 29 mol) is added to a solution of piperazine-1,2,4-(R)-tricarboxylic acid, 1,4-di-tert-butyl ester (2, 3.0 kg) in DMF (22.0 L) at ambient temperature. The resulting mixture is stirred at 20-25° C. for about 30 minutes. The reaction mixture is then cooled to 15-20° C. Methyl iodide (1.0 L; 16 mol) is added, and stirred at 20-25° C. for at least 16 hours. The reaction progress is monitored by TLC (sampling every 1 to 2 hours) and GC-MS. After the reaction is complete, MTBE (17.0 L) is charged and solids are removed by filtration. The filtrate is transferred back to the reactor and cooled to 15-20° C. Water (11.0 L) is added while maintaining the temperature below 15° C. The pH is adjusted to 4-5 by adding 6 N HCl (100.0 mL). The phases are allowed to settle, and the aqueous phase is extracted twice with MTBE (22.0 L each). The MTBE extracts are combined, and washed sequentially with water (22.0 L) and brine (22.0 L). The MTBE phase is dried over MgSO₄, filtered, and concentrated to a residue at about 35° C. under vacuum to remove the MTBE. The solid residue is dried at ambient temperature under vacuum until a constant weight is obtained to afford piperazine-1,2,4-(R)-tricarboxylic acid, 1,4-di-tert-butyl-2-methyl ester (3, 2.5 kg; 100%) as an off-white solid.

Part 4—Preparation of Piperazine-2-(R)-carboxylic acid, methyl ester, dihydrochloride salt (4)

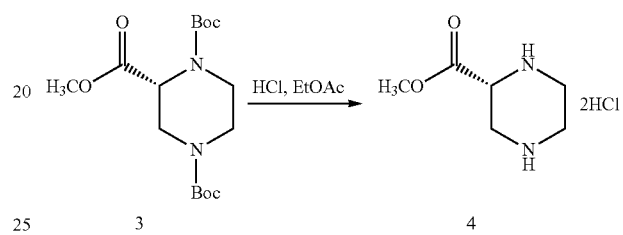

A solution of piperazine-1,2,4-(R)-tricarboxylic acid 1,4-di-tert-butyl-2-methyl ester (3, 1.8 kg, 5.3 moles) in ethyl acetate (33.0 L) is cooled to 15-25° C., and HCl gas (1.5 kg; 41 mol) is charged for approximately 2 hours at a rate such that the batch temperature does not exceed 20-25° C. The progress of the reaction is monitored using TLC and GC-MS. The product crashes out as slurry. After the reaction is complete, the mixture is filtered, and the solids are washed twice with ethyl acetate (13.0 L each wash). The solids are dried at 45-50° C. under vacuum until a constant weight is obtained to afford piperazine-2-(R)-carboxylic acid, methyl ester, dihydrochloride salt (4, 1.1 kg; 85%) as a waxy solid.

Part 5—Preparation of 1-[4-(4-chlorophenoxy)-3,5-difluoro-benzenesulfonyl]-piperazine-2,4-(R)-dicarboxylic acid, 4-(2-methoxy-ethyl)-2-methyl ester (6)

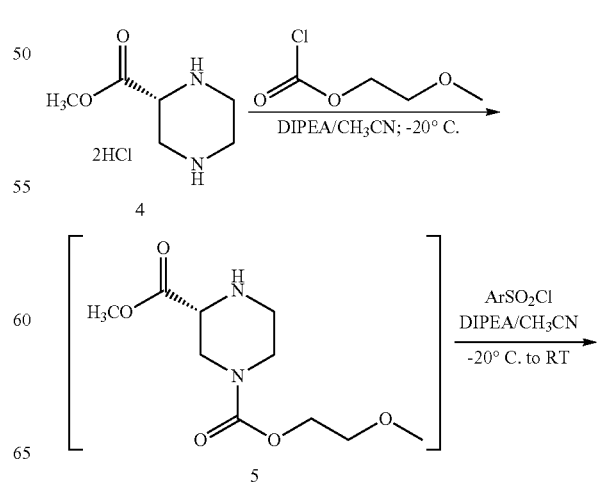

-continued

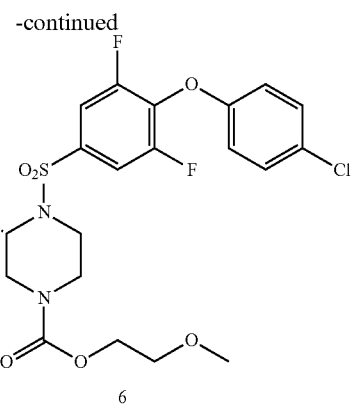

6

Diisopropylethylamine (23.7 kg; 183.7 mol) is added to a solution of piperazine-2-(R)-carboxylic acid, methyl ester, dihydrochloride salt (4, 8.2 kg; 37.8 mol) in acetonitrile (109.5 kg) at a rate such that the temperature does not exceed 25° C. When the addition is complete, the solution is cooled to below −20° C., and a solution of methoxyethyl chloroformate (5.4 kg; 39 mol) in acetonitrile (34.3 kg) is added while maintaining a temperature below −15° C. Agitation is continued for about 30 minutes after completing the addition. The progress of the reaction is monitored by NMR for the formation of the intermediate carbamate 5 (sampled approximately every hour). Alternatively the reaction is monitored by TLC. When no more starting material is observed (1 h after completion of chloroformate addition), diisopropylethylamine (7.85 kg; 61 mol) is added, followed by a solution of 4-(4-chlorophenoxy)-3,5-difluorobenzenesulfonyl chloride (13.9 kg; 41 mol) in acetonitrile (28.6 kg) while maintaining the temperature below −15° C. After the addition, the reaction mixture is warmed to room temperature and held at that temperature until HPLC shows <1% of sulfonyl chloride remaining, ca. 2 h. After the reaction is complete, isopropyl acetate (76 kg) and water (87 kg) are charged sequentially. The biphasic mixture is stirred for approximately 15 minutes and then allowed to settle. The phases are separated, and the organic phase is washed with 1N aqueous HCl (44 kg) followed by water (87 kg), saturated aqueous NaHCO₃ (45 kg), and, finally, brine (45 kg). The isopropyl acetate solution is then dried over Na₂SO₄ (8 kg), filtered, and concentrated at about 45° C. under vacuum to afford crude 1-[4-(4-chloro-phenoxy)-3,5-difluoro-benzenesulfonyl]-piperazine-2, 4-(R)-dicarboxylic acid, 4-(2-methoxy-ethyl)-2-methyl ester as an orange oil (6, 22.4 kg; 108% of theory).

Part 6—Chromatographic Purification of 6

The crude 1-[4-(4-chlorophenoxy)-3,5-difluoro-benzenesulfonyl]-piperazine-2,4-(R)-dicarboxylic acid, 4-(2-methoxy-ethyl)-2-methyl ester (6, 0.9 kg) is applied to the column (silica gel; 6.0 kg) by first dissolving it in ethyl acetate/heptane (500 mL:500 mL). The column is eluted with a mixture of 20% ethyl acetate and heptane (v/v; 5.0 L), followed by a mixture of 25% ethyl acetate and heptane (v/v; 50 L) and, finally, a mixture of 55% ethyl acetate and heptane (v/v; 30.0 L). 2.5 L fractions are collected when the eluent is 20% and 25% ethyl acetate and 5 L fractions are collected later. Each fraction is testeded for the presence of product using TLC, and purity is measured by HPLC. The fractions that contained >95% of product are combined, and the solvent is removed by distillation at about 45° C. under vacuum to afford 6 as a yellow oil at an average of ca. 0.7 kg from each column chromatography (~2.9 kg total yield)

Example 2

Preparation of 4-(4-(4-chlorophenoxy)-3,5-difluorophenylsulfonyl)-3-(hydroxycarbamoyl)piperazine-1-carboxylic acid, (R)-2-methoxyethyl ester (7)

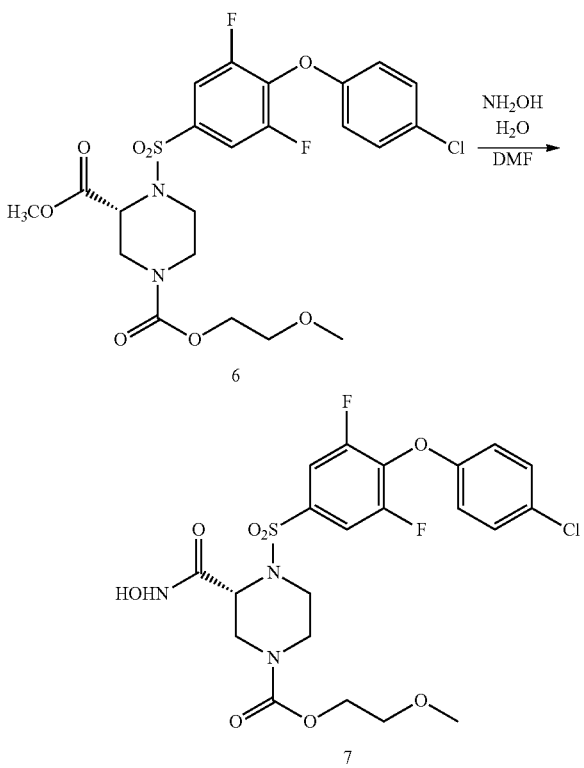

A 50% aqueous solution of hydroxylamine (50%, 14.0 L, 212 mol; 85 eq) is added to a solution of 6 (1.5 kg; 2.73 mol) in DMF (15.0 L) cooled to 15-25° C. The hydroxylamine solution is added at a rate such that the mixture temperature does not exceed 15-25° C. When the addition is complete, the mixture is maintained at 20-25° C. under agitation for a period of approximately 10 hours. The progress of the reaction is monitored using HPLC (the reaction is considered complete when <1.0% of the starting material remained). After the reaction is complete, isopropyl acetate (23.0 L) is added to the mixture, and the aqueous and organic phases are separated. The aqueous phase is extracted with additional isopropyl acetate (23.0 L), and the phases are separated. The combined isopropyl acetate extracts are washed sequentially with brine (8.0 L), aqueous HCl (0.5 N, 8.0 L), ammonium hydroxide (28%, 2×8.0 L), buffer solution (pH 10, 2×8.0 L), and finally with water (8.0 L). The isopropyl acetate is distilled off under vacuum at 45-50° C. Following distillation ethanol (5.0 L) is added to the residue, and distilled off under vacuum at 45-50° C. to afford crude 4-(4-(4-chlorophenoxy)-3,5-difluorophenylsulfonyl)-3-(hydroxycarbamoyl)piperazine-1-carboxylic acid, (R)-2-methoxyethyl ester as a yellow oil. (7, 1.0 kg; 67%).

Example 3

Purification of 4-(4-(4-chlorophenoxy)-3,5-difluorophenylsulfonyl)-3-(hydroxycarbamoyl)piperazine-1-carboxylic acid, (R)-2-methoxyethyl ester via the benzhydrylpiperazine complex Part 1—Preparation of 8

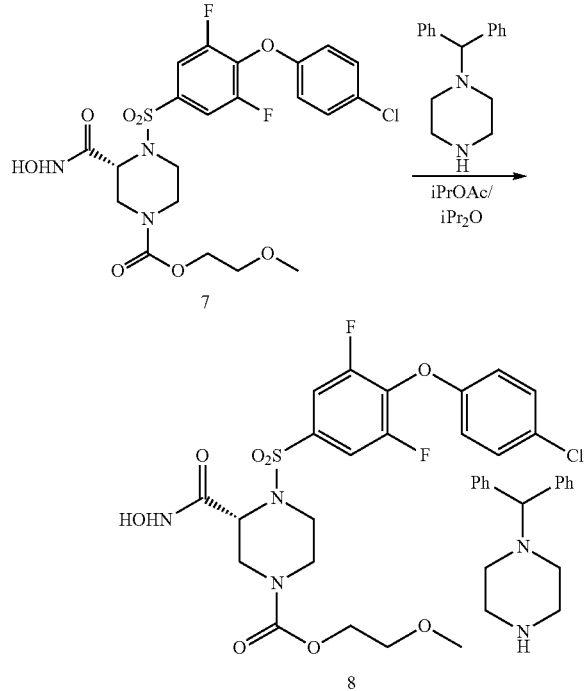

A solution of benzhydrylpiperazine (2.94 kg, 11.6 mol) in isopropyl acetate (14 kg) is added to a solution of crude 7 (6.4 kg, 11.6 mol) in isopropyl acetate (14 kg) and isopropyl ether (11.5 kg). After 30 minutes, isopropyl ether (7 kg) is added and stirred for 2 h at room temperature, and for additional 2 h at 0-5° C. The product is collected by filtration and the filter cake is washed with 4.5 kg of isopropyl ether. The product is dried in a vacuum oven at about 40° C. for 24 h, to yield 7.46 kg (80%) of 8 as colorless crystals.

Part 2—Preparation of 4-(4-(4-chlorophenoxy)-3,5-difluorophenylsulfonyl)-3-(hydroxycarbamoyl)piperazine-1-carboxylic acid (R)-2-methoxyethyl ester magnesium salt/complex (9)

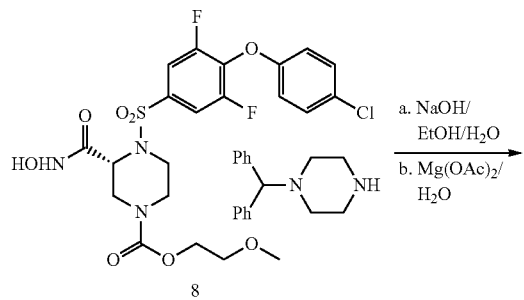

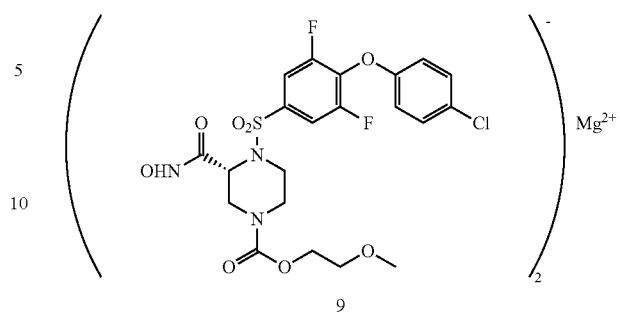

A suspension of 8 (7.46 kg; 9.3 mol) in isopropyl acetate (65 kg) is treated with 0.1 N HCl (126 kg) and stirred for about 15 minutes. The aqueous layer is removed and an additional 60 kg of 0.1 N HCl is added and stirred. The organic layer is washed with 60 kg of water, concentrated under vacuum, dissolved in absolute ethanol (59 kg) and concentrated to an oil under vacuum at 35-40° C. The oil is dissolved in 41 kg of absolute ethanol and cooled to below 25° C. and 2M NaOH solution is added while keeping the temperature below 25° C. After 1 h at room temperature, 20% aqueous Mg(OAc)$_2$ solution is added while keeping the temperature below 25° C. After 30 minutes, water (20 kg) is added and stirred for 2 h. The product is collected by filtration, washed with water, and dried in a vacuum oven at 35-40° C. for 12 h to yield 4.80 kg of 4-(4-(4-chlorophenoxy)-3,5-difluorophenylsulfonyl)-3-(hydroxycarbamoyl)piperazine-1-carboxylic acid (R)-2-methoxyethyl ester magnesium salt (9).

The invention and the manner and process of making and using it, are now described in such full, clear, concise and exact terms as to enable any person skilled in the art to which it pertains, to make and use the same. It is to be understood that the foregoing describes preferred embodiments of the invention and that modifications may be made therein without departing from the spirit or scope of the invention as set forth in the claims. To particularly point out and distinctly claim the subject matter regarded as invention, the following claims conclude this specification.

What is claimed is:

1. A magnesium salt/complex which is

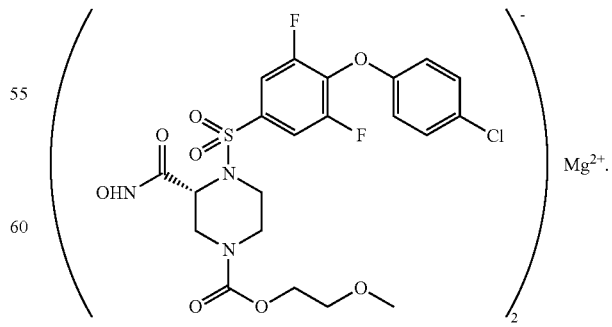

2. A process of preparing a magnesium salt/complex of a compound of formula I:

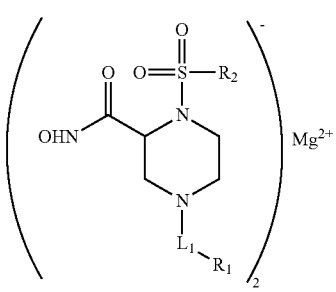

wherein
$L_1$ is —C(O);
$R_1$ is $CH_3$—O—$(CH_2)_2$—O; and
$R_2$ is (4-chloro-phenoxy)-3,5-difluoro-phenyl;
the process comprising:
(i) treating a compound of the formula:

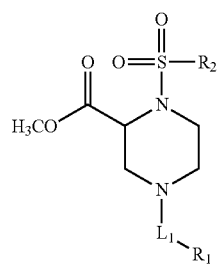

with hydroxylamine to obtain a hydroxycarbamoylpiperazine of the formula:

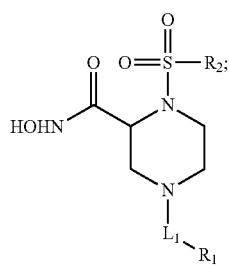

(ii) treating the hydroxycarbamoylpiperazine with benzhydrylpiperazine to obtain a precipitate of the corresponding complex of the formula:

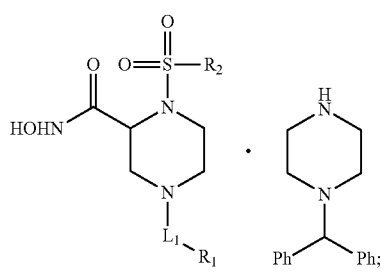

(iii) separating the precipitate from solution; and (iv) treating the precipitate of the complex with base and magnesium salt to obtain the magnesium salt/complex of compound of formula I.

3. The process of claim 2, wherein part (i) employs N,N-dimethylformamide as a solvent.

4. The process of claim 2, wherein the base of part (iv) is alkali metal base.

5. The process of claim 2, wherein the magnesium salt of part (iv) is magnesium acetate.

6. The process of claim 2, wherein part (iv) employs treatment with an acid prior to addition of the base to remove benzyhydrylpiperazine.

7. The process of claim 2, wherein the magnesium salt/complex of a compound of formula I has a purity of at least 99%.

8. A process of purifying and preparing a salt/complex of a compound of formula I:

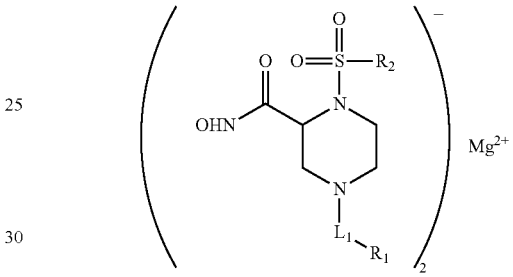

wherein
$L_1$ is —C(O);
$R_1$ is $CH_3$—O—$(CH_2)_2$—O; and
$R_2$ is (4-chloro-phenoxy)-3,5-difluoro-phenyl;
comprising:
(i) treating the compound of formula I with benzhydrylpiperazine to obtain a precipitate of the corresponding complex;

(ii) separating the precipitate from solution; and (iii) treating the precipitate of the complex with base and a salt to yield the salt/complex of the compound.

9. A composition comprising a therapeutically effective amount of the magnesium salt/complex of claim 1 and at least one pharmaceutically acceptable carrier, solvent, adjuvant or diluent.

10. A method of treating arthritis comprising administering to a mammal in need of such treatment a therapeutically effective amount of the compound according to claim 1.

11. A method of treating arthritis comprising administering to a mammal in need of such treatment a therapeutically effective amount of the composition of claim 9.

12. A method of treating lung cancer comprising administering to a mammal in need of such treatment a therapeutically effective amount of the compound according to claim 1.

13. A method of treating lung cancer comprising administering to a mammal in need of such treatment a therapeutically effective amount of the composition of claim 9.

* * * * *

UNITED STATES PATENT AND TRADEMARK OFFICE
CERTIFICATE OF CORRECTION

PATENT NO. : 8,426,415 B2
APPLICATION NO. : 12/682874
DATED : April 23, 2013
INVENTOR(S) : Naganathan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 120 days.

Signed and Sealed this
Fifteenth Day of October, 2013

Teresa Stanek Rea
*Deputy Director of the United States Patent and Trademark Office*